US008809513B2

(12) United States Patent
Wang et al.

(10) Patent No.: US 8,809,513 B2
(45) Date of Patent: Aug. 19, 2014

(54) REVERSE TRANSCRIPTION PRIMERS AND METHODS OF DESIGN

(75) Inventors: Xiaowei Wang, Austin, TX (US);
Xiaohui Wang, Austin, TX (US);
Robert Setterquist, Austin, TX (US)

(73) Assignee: Applied Biosystems, LLC, Carlsbad, CA (US)

( * ) Notice: Subject to any disclaimer, the term of this patent is extended or adjusted under 35 U.S.C. 154(b) by 0 days.

(21) Appl. No.: 13/592,278

(22) Filed: Aug. 22, 2012

(65) Prior Publication Data

US 2013/0059759 A1 Mar. 7, 2013

Related U.S. Application Data

(63) Continuation of application No. 12/950,179, filed on Nov. 19, 2010, now Pat. No. 8,268,987, which is a continuation of application No. 11/566,842, filed on Dec. 5, 2006, now abandoned.

(60) Provisional application No. 60/742,827, filed on Dec. 6, 2005.

(51) Int. Cl.
*C07H 21/04* (2006.01)
*C07H 21/02* (2006.01)
*C40B 40/08* (2006.01)
*C40B 40/06* (2006.01)

(52) U.S. Cl.
CPC *C40B 40/08* (2013.01); *C40B 40/06* (2013.01)
USPC .... 536/24.3; 536/23.1; 536/24.31; 536/24.33

(58) Field of Classification Search
CPC .................................. C40B 40/06; C40B 40/08
See application file for complete search history.

(56) References Cited

U.S. PATENT DOCUMENTS

| | | | |
|---|---|---|---|
| 5,084,565 A | 1/1992 | Parodos et al. |
| 5,324,632 A | 6/1994 | Weisburg et al. |
| 5,401,631 A | 3/1995 | Lane et al. |
| 5,457,025 A | 10/1995 | Collins et al. |
| 5,500,356 A | 3/1996 | Li et al. |
| 5,512,439 A | 4/1996 | Hornes et al. |
| 5,541,308 A | 7/1996 | Hogan et al. |
| 5,554,516 A | 9/1996 | Kacian et al. |
| 5,633,134 A | 5/1997 | Shuber |
| 5,639,428 A | 6/1997 | Cottingham |
| 5,679,520 A | 10/1997 | Hogan et al. |
| 5,708,154 A | 1/1998 | Smith et al. |
| 5,714,324 A | 2/1998 | Kohne |
| 5,723,597 A | 3/1998 | Kohne |
| 5,744,305 A | 4/1998 | Fodor et al. |
| 5,824,517 A | 10/1998 | Cleuziat et al. |
| 5,891,625 A | 4/1999 | Buchardt et al. |
| 5,932,451 A | 8/1999 | Wang et al. |
| 5,948,899 A | 9/1999 | Arnold, Jr. et al. |
| 6,013,440 A | 1/2000 | Lipshutz et al. |
| 6,090,548 A | 7/2000 | Lavery et al. |
| 6,110,678 A | 8/2000 | Weisburg et al. |
| 6,132,997 A | 10/2000 | Shannon |
| 6,150,517 A | 11/2000 | Hogan et al. |
| 6,197,510 B1 | 3/2001 | Vinayagamoorthy |
| 6,203,978 B1 | 3/2001 | Davies et al. |
| 6,221,581 B1 | 4/2001 | Engelhardt et al. |
| 6,228,580 B1 | 5/2001 | Blumenfeld et al. |
| 6,235,483 B1 | 5/2001 | Wolber et al. |
| 6,270,973 B1 | 8/2001 | Lewis et al. |
| 6,294,338 B1 | 9/2001 | Nunomura |
| 6,309,823 B1 | 10/2001 | Cronin et al. |
| 6,316,193 B1 | 11/2001 | He et al. |
| 6,322,971 B1 | 11/2001 | Chetverin et al. |
| 6,329,140 B1 | 12/2001 | Lockhart et al. |
| 6,391,592 B1 | 5/2002 | Su et al. |
| 6,448,387 B1 | 9/2002 | Slater et al. |
| 6,465,183 B2 | 10/2002 | Wolber |
| 6,465,219 B1 | 10/2002 | Zhu |
| 6,495,320 B1 | 12/2002 | Lockhart et al. |
| 6,582,906 B1 | 6/2003 | Cao et al. |
| 7,229,765 B2 | 6/2007 | Ziman et al. |
| 7,601,497 B2 | 10/2009 | Nazarenko et al. |
| 8,268,987 B2 | 9/2012 | Wang et al. |
| 2001/0026919 A1 | 10/2001 | Chenchik et al. |
| 2002/0072061 A1 | 6/2002 | Chenchik et al. |
| 2002/0076767 A1 | 6/2002 | Su et al. |
| 2003/0022318 A1 | 1/2003 | Lin et al. |
| 2003/0073081 A1 | 4/2003 | Mukai et al. |

(Continued)

FOREIGN PATENT DOCUMENTS

| | | |
|---|---|---|
| EP | 0787209 | 3/2002 |
| EP | 1463835 | 7/2003 |
| EP | 1871913 | 1/2008 |
| EP | 1941058 | 7/2008 |
| EP | 1957645 | 8/2008 |

(Continued)

OTHER PUBLICATIONS

Affymetrix Technical Notes, , "Globin reduction protocol: a method for processing whole blood RNA samples for improved array results", *Gene Expression Monitoring*, 2003, 1-10.

Ahern, "Biochemical, Reagent Kits Offer Scientists Good Return on Investment", *The Scientist*, vol. 9, No. 15, Jul. 24, 2005, 20-24.

Ambion, Inc., "Unmask blood RNA for gene expression profiling", www.biocompare.com/techncialarticle/1056/unmask-blood-RNA-for-gene-expression-rpofiling-from-Ambion.html, Oct. 31, 2009, 1-4.

Armour et al., "Digital transcriptome profiling using selective hexamer priming for cDNA synthesis", *Nature Methods*, vol. 6, No. 9, Sep. 1, 2009, 647-649.

(Continued)

*Primary Examiner* — James Martinell

(57) ABSTRACT

The present invention provides novel algorithms for designing oligonucleotides that do not substantially hybridize to a small group of unwanted transcripts, while hybridizing to most other transcripts. Such oligonucleotides are particularly useful as primers for reverse transcription. The invention also provides compositions containing oligonucleotides that do not substantially hybridize to a small group of unwanted transcripts, while hybridizing to most other transcripts.

19 Claims, 8 Drawing Sheets

(56) References Cited

U.S. PATENT DOCUMENTS

| | | | |
|---|---|---|---|
| 2003/0073112 A1 | 4/2003 | Zhang et al. | |
| 2003/0104432 A1 | 6/2003 | Xu et al. | |
| 2003/0119047 A1 | 6/2003 | Yoshikawa et al. | |
| 2003/0152925 A1 | 8/2003 | Chun | |
| 2004/0014105 A1 | 1/2004 | Schroeder et al. | |
| 2004/0081978 A1 | 4/2004 | Ziman et al. | |
| 2004/0086913 A1* | 5/2004 | Williams et al. | 435/6 |
| 2005/0003369 A1 | 1/2005 | Christians et al. | |
| 2006/0257902 A1 | 11/2006 | Mendoza et al. | |
| 2007/0255053 A1 | 11/2007 | Ziman et al. | |
| 2008/0187969 A1* | 8/2008 | Castle et al. | 435/91.2 |
| 2009/0264635 A1 | 10/2009 | Mendoza et al. | |
| 2010/0029511 A1 | 2/2010 | Raymond et al. | |

FOREIGN PATENT DOCUMENTS

| | | |
|---|---|---|
| WO | WO99/11823 | 3/1999 |
| WO | WO99/14226 | 3/1999 |
| WO | WO01/09310 | 2/2001 |
| WO | WO01/32672 | 5/2001 |
| WO | WO01/71036 | 9/2001 |
| WO | WO02/44399 | 6/2002 |
| WO | WO03/054162 | 7/2003 |
| WO | WO2005/003370 | 1/2005 |
| WO | WO2007/050990 | 5/2007 |
| WO | WO2007/067907 | 6/2007 |
| WO | WO2009/055732 | 4/2009 |

OTHER PUBLICATIONS

Brown et al., "Targeted display: a new technique for the analysis of differential gene expression", *Methods in Enzymology*, vol. 303, Jan. 1, 1999, 392-408.

Caetano-Anolles et al., "DNA Amplification Fingerprinting Using Very Short Arbitrary Oligonucleotides", *Bio/Technology*, vol. 9, No. 6, Jun. 1, 1991, 553-557.

Consalez et al., "A computer-driven approach to PCR-based differential screening, alternative to differential display", *BioInformatics*, vol. 15, No. 2, Feb. 1, 1999, 93-105.

EP Application No. 06758207.2, Office Action mailed Jul. 28, 2008.
EP Application No. 06758207.2, Office Action mailed Jul. 6, 2009.
EP Application No. 06827033.9, Supplementary European Search Report mailed Dec. 22, 2009.
EP 0 Application No. 6846486.6, Office Action mailed Mar. 18, 2009.
International Application No. PCT/US2001/044821, International Preliminary Examination Report mailed Feb. 12, 2003.
International Application No. PCT/US2001/044821, International Search Report mailed Dec. 13, 2002.
International Application No. PCT/US2002/041014, International Preliminary Examination Report mailed Mar. 5, 2004.
International Application No. PCT/US2002/041014, International Search Report mailed Jul. 16, 2003.
International Application No. PCT/US2006/011185, International Preliminary Report mailed Sep. 25, 2007.
International Application No. PCT/US2006/011185, International Search Report and Written Opinion mailed Dec. 12, 2006.
International Application No. PCT/US2006/042250, International Preliminary Report mailed Apr. 29, 2008.
International Application No. PCT/US2006/042250, International Search Report and Written Opinion mailed Sep. 21, 2007.
International Application No. PCT/US2006/061643, International Preliminary Report mailed Jun. 11, 2008.
International Application No. PCT/US2006/061643, International Search Report and Written Opinion mailed May 14, 2007.
International Application No. PCT/US2008/081206, International Preliminary Examination Report mailed Apr. 27, 2010.
International Application No. PCT/US2008/081206, International Search Report and Written Opinion mailed on Mar. 23, 2009.

Kim et al., "Octamer-based genome scanning distinguishes a unique subpopulation of *Escherichia coli* 0157 :H7 strains in cattle", *Proceedings of the National Academy of Sciences*, vol. 96, No. 23, 1999, 13288-13293.

Lopez-Nieto et al., "Selective amplification of protein-coding regions of large sets of genes using statistically designed primer sets", *Nature Biotechnology*, vol. 14, No. 7, Jul. 1, 1996, 857-861.

Niedhardt, "*Escherichia coli* and *Salmonella*", ASM Press, vol. 1, 1996, 13-16.

Pesole, et al., "GeneUp: a program to select short PCR primer pairs that occur in multiple members of sequence lists", *Biotechniques*, vol. 25, No. 1, Jul. 1, 1998, 112-123.

Roberts, et al., "Signaling and Circuitry of Multiple MAPK Pathways Revealed by a Matrix of Global Gene Expression Profiles", *Science*, vol. 287, 2000, 873-880.

Robinson, et al., "Isolation of maltose-regulated genes from the hyperthermophilic archaem, *Pyrococcus furiosus*, by substractive hybridization", *Gene*, vol. 148, 1994, 137-141.

Sarin et al., "Inhibition of Acquired Immunodeficiency Syndrome Virus by Oligodeoxynucleoside Methylphosphonates", *Proceedings of the National Academy of Sciences*, vol. 85, No. 20, Oct. 15, 1988, 7448-7451.

Stahlberg et al., "Properties of the reverse transcription reaction in mRNA quantification", *Clinical Chemistry*, vol. 50, No. 3, Mar. 1, 2004, 509-515.

Stein et al., "Physicochemical Properties of Phosphorothioate Oligodeozynucleotides", *Nucleic Acids Research*, vol. 16, No. 8, 1988, 3209-3221.

Unknown, "New products", *Science Magazine*, vol. 310, 2005, 873.
U.S. Appl. No. 10/029,397, Advisory Action Before Filing Appeal Brief mailed Feb. 11, 2005.
U.S. Appl. No. 10/029,397, Advisory Action Before Filing Appeal Brief mailed Mar. 8, 2005.
U.S. Appl. No. 10/029,397, Advisory Action mailed Nov. 23, 2004.
U.S. Appl. No. 10/029,397, Final Office Action mailed Sep. 1, 2004.
U.S. Appl. No. 10/029,397, Non-Final Office Action mailed Mar. 11, 2005.
U.S. Appl. No. 10/029,397, Office Action mailed Jun. 26, 2003.
U.S. Appl. No. 10/029,397, Office Action mailed Mar. 11, 2004.
U.S. Appl. No. 10/029,397, Response to Final Office Action and Notice of Appeal filed Dec. 3, 2004.
U.S. Appl. No. 10/029,397, Response to Final Office Action filed Nov. 4, 2004.
U.S. Appl. No. 10/029,397, Response to Office Action filed Aug. 4, 2003.
U.S. Appl. No. 10/029,397, Response to Office Action filed Jun. 11, 2004.
U.S. Appl. No. 10/029,397, Response to Office Action mailed Feb. 18, 2005.
U.S. Appl. No. 10/029,397, Response to Restriction Requirement filed Jan. 27, 2003.
U.S. Appl. No. 10/029,397, Response to Restriction Requirement filed Mar. 25, 2003.
U.S. Appl. No. 10/029,397, Response to Restriction Requirement filed May 6, 2003.
U.S. Appl. No. 10/029,397, Restriction Requirement mailed Apr. 22, 2003.
U.S. Appl. No. 10/029,397, Restriction Requirement mailed Feb. 21, 2003.
U.S. Appl. No. 10/029,397, Restriction Requirement mailed Jan. 13, 2003.
U.S. Appl. No. 11/389,876, Office Action mailed May 10, 2007.
U.S. Appl. No. 11/389,876, Response to Restriction Requirement filed Feb. 22, 2007.
U.S. Appl. No. 11/389,876, Restriction Requirement mailed Jan. 30, 2007.
U.S. Appl. No. 11/589,322, Final Office Action mailed Aug. 20, 2009.
U.S. Appl. No. 11/589,322, Office Action mailed Jan. 29, 2009.
U.S. Appl. No. 11/589,322, Office Action mailed Apr. 8, 2010.
U.S. Appl. No. 11/589,322, Request for Continued Examination with Amendment filed Jan. 20, 2010.

(56) References Cited

OTHER PUBLICATIONS

U.S. Appl. No. 11/589,322, Response to Office Action mailed Apr. 29, 2009.
U.S. Appl. No. 11/589,322, Response to Restriction Requirement filed Nov. 26, 2008.
U.S. Appl. No. 11/589,322, Restriction Requirement mailed Aug. 26, 2008.
U.S. Appl. No. 11/745,386, Final Office Action mailed Jul. 2, 2009.
U.S. Appl. No. 11/745,386, Office Action mailed on Dec. 29, 2009.
U.S. Appl. No. 11/745,386, Response to Office Action mailed Sep. 28, 2009.
Velculescu et al., "Serial Analysis of Gene Expression", *Science*, vol. 270, No. 5235, 1995, 484-487.
Wang et al., "A PCR primer bank for quantitative gene expression analysis", *Nucleic Acid Research*, vol. 31, No. 24, Dec. 15, 2003, e154.
Wang et al., "Selection of oligonucleotide probes for protein coding sequences", *BioInformatics*, vol. 19, No. 7, May 1, 2003, 796-802.
Wendisch et al., "Isolation of *Escherichia coli* mRNA and comparison of expression using mRNA and total RNA on DNA microarrays", *Analytical Biochemistry*, vol. 290, 2001, 205-213.
Wong et al., "Use of Tagged Random Hexamer Amplification (TRHA) to Clone and Sequence Minute Quantities of DNA—Application to a 180 kb Plasmid Isolated from Sphingomonas F199", *Nucleic Acids Research*, vol. 24, No. 19, 1996, 3778-3783.
Zhang et al., "Differential priming of RNA templates during cDNA synthesis markedly affects both accuracy and reproducibility of quantitative competitive reverse-transcriptase PCR", *Biochemical Journal*, vol. 337, No. 2, Jan. 15, 1999, 231-241.

\* cited by examiner

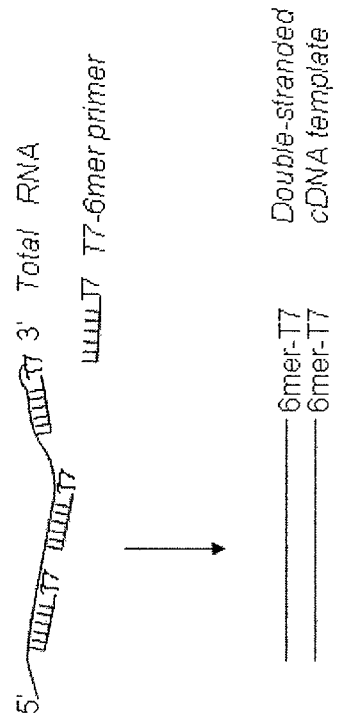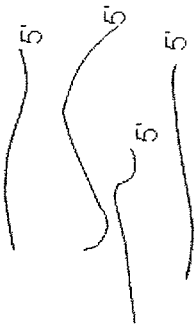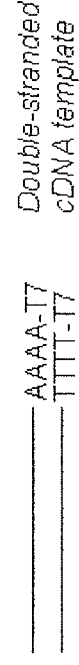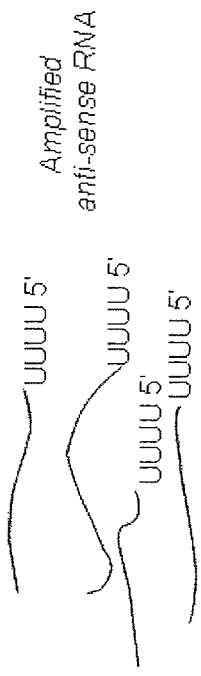
FIGs. 6A - 6B

REVERSE TRANSCRIPTION PRIMERS AND METHODS OF DESIGN

This application is a continuation of U.S. application Ser. No. 12/950,179 filed Nov. 19, 2010 now U.S. Pat. No. 8,268,987, which is a continuation of U.S. application Ser. No. 11/566,842 filed Dec. 5, 2006 now abandoned and claims priority to U.S. Application No. 60/742,827 filed Dec. 6, 2005, which disclosures are herein incorporated by reference in their entirety.

BACKGROUND OF THE INVENTION

1. Field of the Invention

The present invention relates generally to the field of molecular biology. More particularly, it concerns the selection of reverse transcription primer pools to avoid amplification of a small group of unwanted transcripts, while reverse transcribing most other transcripts in a sample.

2. Description of Related Art

With the advent of novel high-throughput approaches, such as microarrays, researchers can now measure changes of the expression profiles of thousands of genes in a single experiment. As the first step, RNAs of interest are usually converted to cDNA. This conversion is performed with a reverse transcription (RT) reaction. Currently two types of oligonucleotides primers, oligo dT and random hexamers are commonly used to anneal to RNA molecules to start the RT reactions. Unfortunately, both priming methods have major limitations.

Random primers are commonly used in RT reactions for total RNA. Typically, most of the RNA in a sample is rRNA, whereas other transcripts (e.g. mRNAs) comprise only a small percentage of total RNA. As a result, the overwhelming majority of final cDNA products are from rRNAs. The presence of these rRNA-derived products may be detrimental to many downstream applications. For example, background signals increase significantly in microarray hybridizations in the presence of cDNA products from rRNAs. Removing rRNA prior to microarray hybridization results in a higher percentage of present calls, which is an indication of better array sensitivity. rRNA removal also results in increased sample correlations/concordance among array replicates. The benefit of rRNA removal is even more obvious for amplified RNA samples.

Various methods have been applied for rRNA removal. For example, Affymetrix Inc. introduced a procedure for removing rRNA by enzymatic digestions. However, the whole procedure is both time consuming and expensive to researchers. Alternatively, mRNA may be enriched by removing rRNA molecules with magnetic beads. rRNA specific oligonucleotide probes are attached to magnetic beads, which are incubated with total RNA. In this way, rRNA is captured by the beads and later removed by centrifugation. Ambion provides a kit for the removal of bacterial RNA (MICROBExpress); the Ribo-Minus kit is available from Invitrogen for human and mouse rRNA removal. Thus, while it is possible to deplete rRNA from a sample, the extra step of rRNA removal can complicate experiments and introduce additional cost.

In contrast to the random priming strategy, oligo-d(T) priming is widely used to enrich the mRNA population directly. Oligo dT primers anneal specifically to the poly(A) tail of mRNA molecules, and thus reverse transcription of rRNA is minimized. However, oligo d(T) primers are not suitable for all applications. For example, oligo d(T) are not suitable as RT primers for bacterial mRNA because most of them do not have poly(A) tails. In addition, many other interesting non-coding RNAs in the transcriptome, such as microRNAs (miRNAs) and siRNAs will not be covered. Partially degraded RNAs also cannot be fully transcribed using oligo d(T) primers. Degraded RNA is commonly encountered with most clinical human samples such as RNA collected from Formalin Fixed Paraffin Embedded (FFPE) samples or from tissues rich in nucleases.

In addition, the oligo-d(T) priming strategy introduces 3' bias in cDNA synthesis because it is difficult to produce full-length cDNAs due to the limited RT extension capability. This is an especially serious problem for RT-based linear RNA amplification since only about 1 kilobase of 3' sequences can be effectively amplified. In view of this problem, most microarray platforms are designed for the 3' regions of the transcripts. For example, many Affymetrix probes are picked from the last 600 bases of the mRNA sequences. Unfortunately, this size limitation is a major drawback because researchers are unable to examine relevant biological information, such as alternative splicing, from the entire transcriptome. Affymetrix has launched a new GeneChip platform—whole genome tiling arrays, which are designed for profiling of the entire transcriptome. However, most existing RNA amplification products for GeneChips use oligo-d(T) as the RT primer and thus will not be suitable for the new full-transcript coverage arrays.

SUMMARY OF THE INVENTION

The present invention provides novel methods for designing oligonucleotides and novel oligonucleotide compositions that are useful in a variety of applications including, for example, reverse transcription, RNA amplification, and microarray analysis. In one embodiment, the present invention provides a method of designing a pool of oligonucleotides that do not substantially hybridize to one or more unwanted sequences, the method comprising: selecting at least one exclusion sequence to which hybridization of a pool of oligonucleotides having hybridization sequences of length n is not desired; employing a selection method to determine which hybridization sequences of length n are not expected to substantially hybridize to the exclusion sequence; and identifying a pool of oligonucleotides comprising a plurality of oligonucleotides having non-identical hybridization sequences of length n that do not substantially hybridize to the exclusion sequence.

The selection method may be, for example, a computational selection method. A computational selection method may be used to select or design oligonucleotides in silico. A computational selection method may employ, for example, an algorithm having one or more selection filters to select or design the desired oligonucleotides. In one embodiment, the computational selection method comprises: identifying a set of all possible sequences of length n; identifying a set of all sequences of length n contained in the exclusion sequence; comparing the set of sequences of length n contained in the exclusion sequence to the set of all possible sequences of length n; and excluding from the pool of oligonucleotides those oligonucleotides having at their 3' end a sequence of length n that is identical to a sequence of length n contained in the exclusion sequence. In certain aspects the method may comprise the step of retaining in the pool of oligonucleotides those oligonucleotides having at their 3' end a sequence of length n that has at least 2 mismatches when compared to the set of all sequences of length n contained in the exclusion sequence. In some aspects the method may comprise the step of excluding from the pool of oligonucleotides those oligonucleotides in which the only mismatch is a GU at the 5' end of the sequence of length n and the rRNA hits are greater than 3 or mRNA hits are less than 3000. The hits to rRNAs are defined as the number of primer matches to rRNA sequences with the only mismatch as a GU wobble pair. The hits to mRNAs are defined as the number of occurrences of oligos perfectly matching an mRNA sequence. Each mRNA is counted only once. In some aspects the method may comprise assessing binding free energy (ΔG) of the oligonucleotides and excluding from the pool of oligonucleotides those oligonucleotides having low ΔG. In a preferred embodiment, the threshold value −8 kcal/mol is used as the cutoff such that all selected primers have a binding free energy greater than the threshold value. In certain aspects of the invention, the threshold value for binding free energy may be −5 kcal/mol, −6 kcal/mol, −7 kcal/mol, −8 kcal/mol, −9 kcal/mol, or −10 kcal/mol. The binding free energy value may be calculated as described, for example, in Sugimoto et al. (1995).

In other aspects of the invention, the selection method may be a physical selection method. For example, in one embodiment, the physical selection method may comprise: contacting a candidate population of oligonucleotides with a substrate on which the exclusion sequence or one or more fragments of length n of the exclusion sequence is immobilized; and retaining oligonucleotides that do not exhibit specific binding affinity to the exclusion sequence. The substrate on which the exclusion sequence is immobilized may be, for example, a column, bead, membrane, or chip.

In one embodiment, the present invention provides a composition comprising a pool of at least 15 oligonucleotide primers having non-identical hybridization sequences of length n, wherein the hybridization sequences do not substantially hybridize to an exclusion sequence. In some embodiments, the composition comprises a pool of at least 20, 30, 40, 50, 60, 70, 80, 90, 100, 150, 200, 250, 300, 350, 400, 500, 600, 700, 800, 900, 1000, 1250, 1500, 1750, 2000, 2500, 3000, 4000, 5000, 6000, 7000, 8000, 9000, 10000, 15000, 20000, 30000, 40000, 50000, 60000, 70000, 80000, 90000, 100000, 110000, 120000, 130000, 140000, or 150000 oligonucleotide primers having non-identical hybridization sequences of length n, wherein the hybridization sequences do not substantially hybridize to an exclusion sequence. Of course, it will be understood by those in the art that the maximum number of non-identical sequences of length n will be dependent on the value of n. For example, there are 4,096 possible sequences for a sequence that is 6 nucleotides in length and there are 262,144 possible sequences for a sequence that is 9 nucleotides in length. In some embodiments, the composition comprises a pool of between about 15 to 150000, 15 to 5000, 50 to 150000, 50 to 5000, 50 to 2500, 100 to 2500, 100 to 2000, 100 to 1500, 100 to 400, 200 to 2000, 300 to 150000, 300 to 1500, 800 to 6000, 2000 to 20000, or any range therein, of oligonucleotide primers having non-identical hybridization sequences of length n, wherein the hybridization sequences do not substantially hybridize to an exclusion sequence. In some embodiments, the composition may further comprise an oligo-dT primer. In a preferred embodiment, the oligo-dT primer comprises a sequence having between 5 to 60 contiguous thymidines. The molar ratio of the oligo-dT primer to the oligonucleotide primers having non-identical hybridization sequences may be between about 1:1000 to about 2:1, or any range derivable therein. In certain embodiments the molar ratio of the oligo-dT primer to the oligonucleotide primers having non-identical hybridization sequences may be 1:100 to about 3:2, or any range derivable therein. Preferably, the molar ratio of the oligo-dT primer to the oligonucleotide primers having non-identical hybridization sequences is about 1:100 to about 1:5.

A sequence of length n may comprise any length of nucleotides. In some embodiments, the length n is defined as between 4 to 11 nucleotides or any range derivable therein. In a preferred embodiment, the length n is defined as between 5 to 9 nucleotides. More preferably, the length n is defined as between 5 to 7 nucleotides. In certain embodiments, the length n is defined as 4, 5, 6, 7, 8, 9, 10, or 11 nucleotides, or any range therein. The total number of unique sequences of length n can be determined using the formula $4^n$. For example, if the length n equals 6, the total number of unique sequences is $4^6$ or 4,096.

An "exclusion sequence" may be any sequence or sequences to which hybridization of an oligonucleotide or pool of oligonucleotides is not desired. In certain aspects of the invention, the exclusion sequence may be, for example, an rRNA sequence a tRNA sequence or another abundant RNA transcript. Another example of an abundant RNA transcript is globin mRNA. Globin mRNA constitutes 70% of total mRNA isolated from whole blood. The presence of globin mRNA can significantly affect expression analysis of other genes in microarray experiments. By designing primers that do not efficiently reverse transcribe globin mRNA, background noise can be significantly reduced resulting in increased detection sensitivity in blood transcriptional studies.

In one embodiment, the present invention provides a method of obtaining cDNA with substantially no contaminating rRNA-derived sequences comprising: obtaining a pool of primers having non-identical hybridization sequences of length n, wherein the hybridization sequences are selected such that they do not substantially hybridize to an rRNA sequence; obtaining an RNA-containing sample; and combining the pool of primers and the RNA-containing sample under conditions conducive to reverse transcription of RNA in the RNA-containing sample initiated from the pool of primers; and obtaining cDNA with substantially no contaminating rRNA-derived sequences.

The rRNA-derived sequence may be any sequence derived from rRNA. The rRNA sequence may be eukaryotic rRNA, such as 28S, 18S, or 5.8S rRNA, or prokaryotic rRNA, such as 16S or 23S rRNA.

An RNA-containing sample may be any sample that comprises RNA. The sample may be obtained from, for example, a cell, cell culture, a body fluid, a tissue, or an organ. In certain embodiments, the sample is a fixed sample or a frozen sample, such as a fixed tissue or frozen tissue sample. In some embodiments, the sample is a formalin fixed paraffin embedded (FFPE) sample. The sample may be an environmental sample. Examples of environmental samples include soil samples, water samples, and air samples.

The "transcriptome" refers to the complete collection of transcribed elements of the genome. The transcriptome represents mRNAs as well as non-coding RNAs (e.g., rRNA, miRNA, siRNA). In certain embodiments, oligonucleotide primers according to the present invention allow for synthesis of cDNA from a majority of non-ribosomal RNAs in the RNA-containing sample. Non-ribosomal RNAs include, for example, mRNA, miRNA, and siRNA. In some embodiments, oligonucleotide primers according to the present invention allow for synthesis of cDNA having substantially no contaminating rRNA-derived sequences. cDNA having substantially no contaminating rRNA-derived sequences may be defined as cDNA in which less than about 50%, 40%, 30%, 25%, 20%, 15%, 10%, 9%, 8%, 7%, 6%, 5%, 4%, 3%, 2%, 1%, 0.8%, 0.5%, or 0.2% of the cDNA is synthesized from an rRNA sequence.

In some embodiments, oligonucleotide primers according to the present invention allow for synthesis of cDNA representative of at least 50%, 60%, 70%, 75%, 80%, 85%, 90%, 95%, 96%, 97%, 98%, 99%, 99.2%, 99.5%, 99.8%, or 99.9% of the mRNA sequences present in an RNA-containing sample. In one embodiment, oligonucleotide primers according to the present invention allow for synthesis of cDNA representative of at least about 75% of the mRNA sequences in the RNA-containing sample, and wherein less than about 10% of the cDNA is synthesized from an rRNA sequence.

In one embodiment, the invention provides a set of oligonucleotides comprising sequences of Sequence #s 1 to 1152 as defined in Table 1 below. In another embodiment, the invention provides a set of oligonucleotides comprising sequences of Sequence #s 1 to 379 as defined in Table 1 below. In yet another embodiment, the invention provides a set of oligonucleotides comprising sequences of Sequence #s 380 to 1152 as defined in Table 1 below. In certain aspects of the invention there is provided a composition comprising 15 or more, 25 or more, 50 or more, 100 or more, 150 or more, 200 or more, 250 or more, 300 or more, 400 or more, 500 or more, 600 or more, 700 or more, 800 or more, 900 or more, or 1000 or more of the oligonucleotides selected from the group consisting of Sequence #s 1 to 1152 as defined in Table 1 below.

TABLE 1

| Seq. # | Sequence |
|---|---|
| 1 | AAATAA |
| 2 | AAAATG |
| 3 | AAAATT |
| 4 | TAAATA |
| 5 | TAATAA |
| 6 | AATAAG |
| 7 | AAATAT |
| 8 | AAATAC |
| 9 | TATAAG |
| 10 | ATATAA |
| 11 | AAATTG |
| 12 | ATAATA |
| 13 | AAACAA |
| 14 | AAATTT |
| 15 | CAAAAC |
| 16 | CAAATA |
| 17 | CAATAA |
| 18 | TATATA |
| 19 | AATTAT |
| 20 | AATTTA |
| 21 | TGAAAT |
| 22 | AAATGA |
| 23 | GAAATT |

TABLE 1-continued

| Seq. # | Sequence |
|---|---|
| 24 | AATATC |
| 25 | ATATAG |
| 26 | ATATAT |
| 27 | AACAAG |
| 28 | ATTATA |
| 29 | GTAAAG |
| 30 | TGTAAA |
| 31 | ATAAGA |
| 32 | AGATAA |
| 33 | CAATAT |
| 34 | AAACAC |
| 35 | GAATAC |
| 36 | AAATGG |
| 37 | ACATAA |
| 38 | ATACAA |
| 39 | ACAATA |
| 40 | AGAATG |
| 41 | AAATCT |
| 42 | TAGTAA |
| 43 | GTATAA |
| 44 | AACATA |
| 45 | AAGATG |
| 46 | TATAGA |
| 47 | GAATTG |
| 48 | AAGATT |
| 49 | TTTTAG |
| 50 | TTTTAT |
| 51 | TACAAC |
| 52 | AACTAT |
| 53 | CAATTG |
| 54 | AATGAC |
| 55 | AAGTAT |
| 56 | AATGTA |
| 57 | GTAATG |
| 58 | CAATTT |
| 59 | AACGAA |
| 60 | AAAGTC |
| 61 | ATAAGG |
| 62 | TGTAAG |

TABLE 1-continued

| Seq. # | Sequence |
|---|---|
| 63 | AGTAAG |
| 64 | AACTTA |
| 65 | CAAACA |
| 66 | ATGTAA |
| 67 | ATAAGT |
| 68 | ATATGA |
| 69 | AATCTA |
| 70 | AGATAT |
| 71 | ACAATT |
| 72 | CAAACG |
| 73 | CTATAG |
| 74 | TATGAT |
| 75 | ATAGAG |
| 76 | CGTAAA |
| 77 | AAGTAC |
| 78 | CGAATA |
| 79 | CGATAA |
| 80 | TGATAC |
| 81 | AACTTG |
| 82 | AGATAC |
| 83 | ATACTA |
| 84 | TACTAT |
| 85 | TGAAGA |
| 86 | GAATGA |
| 87 | TAACTC |
| 88 | ACATAT |
| 89 | AACATC |
| 90 | ATGATG |
| 91 | AATGTT |
| 92 | AATTGG |
| 93 | ATACAG |
| 94 | ACATAG |
| 95 | TAACGA |
| 96 | TGTATA |
| 97 | AATTGT |
| 98 | CAAGAG |
| 99 | AATTCG |
| 100 | AGATTG |
| 101 | AATAGC |

TABLE 1-continued

| Seq. # | Sequence |
|---|---|
| 102 | TAGTAC |
| 103 | TGACAA |
| 104 | CTGAAT |
| 105 | ACAAGA |
| 106 | TAATGC |
| 107 | AAACGT |
| 108 | TCATAT |
| 109 | ATACTG |
| 110 | GTAAGA |
| 111 | AAACGG |
| 112 | ACAGAA |
| 113 | AACAGA |
| 114 | TAAGGA |
| 115 | CAGAAC |
| 116 | ATACTT |
| 117 | CAGTAA |
| 118 | TTCATA |
| 119 | AACGAG |
| 120 | ACTATT |
| 121 | ATGTAG |
| 122 | TAGAGA |
| 123 | ATTACT |
| 124 | TATGTG |
| 125 | GAGATA |
| 126 | AAATCC |
| 127 | ATCTAT |
| 128 | ATGTTA |
| 129 | CAGATA |
| 130 | TTGTAG |
| 131 | AAGTGA |
| 132 | ACACAA |
| 133 | ACATTT |
| 134 | AAAGCA |
| 135 | CACAAC |
| 136 | CAATCA |
| 137 | CGATAT |
| 138 | AACGAC |
| 139 | TAACGT |
| 140 | GATACA |

TABLE 1-continued

| Seq. # | Sequence |
|---|---|
| 141 | AACGTA |
| 142 | TATAGC |
| 143 | ATAACC |
| 144 | ATGAGA |
| 145 | ACGTAA |
| 146 | ACAACG |
| 147 | GACATA |
| 148 | AAAGCT |
| 149 | CATGAT |
| 150 | ACGATA |
| 151 | ATGTTG |
| 152 | TACGAT |
| 153 | ACAACT |
| 154 | TCTATC |
| 155 | TAAGGT |
| 156 | ACAAGG |
| 157 | ACAAGT |
| 158 | CGTATA |
| 159 | ATGACA |
| 160 | CCAAAC |
| 161 | GTAGAG |
| 162 | ACAGAG |
| 163 | TGTAGA |
| 164 | GAAGTC |
| 165 | GATGTA |
| 166 | AACTCA |
| 167 | GTATGA |
| 168 | TGAGTA |
| 169 | CTAGTA |
| 170 | CGATTG |
| 171 | CAACTC |
| 172 | CACTAT |
| 173 | ACATGA |
| 174 | GCATAA |
| 175 | CAACGA |
| 176 | CAAGTC |
| 177 | AACGTT |
| 178 | CAGTAT |
| 179 | AACTGG |

TABLE 1-continued

| Seq. # | Sequence |
|---|---|
| 180 | GATCTA |
| 181 | AACTGT |
| 182 | AAACCG |
| 183 | AAAGGC |
| 184 | AACTCG |
| 185 | CATAGG |
| 186 | CGAACA |
| 187 | AATCGT |
| 188 | TCATGA |
| 189 | TGAAGC |
| 190 | GAGTAC |
| 191 | CTCATA |
| 192 | AGACAC |
| 193 | GGATAC |
| 194 | TCAGAT |
| 195 | ACACTA |
| 196 | ACGATT |
| 197 | GTACTA |
| 198 | CCAATA |
| 199 | CAATGC |
| 200 | ATGTGA |
| 201 | CAAGGA |
| 202 | ACAGTA |
| 203 | AGGATG |
| 204 | TGATGG |
| 205 | ATGAGT |
| 206 | CGTTAG |
| 207 | ACACAG |
| 208 | AAGTCT |
| 209 | TGATGT |
| 210 | ACTTGA |
| 211 | AGCAAG |
| 212 | CTGTAG |
| 213 | GTACAG |
| 214 | CTAGTG |
| 215 | GATTGT |
| 216 | ACGTAG |
| 217 | GGATTG |
| 218 | CCTAAT |

TABLE 1-continued

| Seq. # | Sequence |
|---|---|
| 219 | ACTACT |
| 220 | ACGTAT |
| 221 | AACGTC |
| 222 | CAGTTG |
| 223 | GGAACA |
| 224 | ACACTG |
| 225 | AACAGC |
| 226 | GCTATA |
| 227 | ATCGTA |
| 228 | ACACTT |
| 229 | ATATCC |
| 230 | GACAGA |
| 231 | ACCTAA |
| 232 | GATAGC |
| 233 | CTCTAC |
| 234 | AGGTAT |
| 235 | AACCTA |
| 236 | TGTAGT |
| 237 | TAGCAG |
| 238 | ATCACT |
| 239 | AGTCTA |
| 240 | CAACGT |
| 241 | TGCATA |
| 242 | ACCAAT |
| 243 | ATAGCA |
| 244 | ACGAGA |
| 245 | TCTAGT |
| 246 | TTAGGT |
| 247 | CGGTAA |
| 248 | CATAGC |
| 249 | TGTCAT |
| 250 | CGTAGA |
| 251 | AGGTAC |
| 252 | CACGAT |
| 253 | ACTTCA |
| 254 | ATAGCG |
| 255 | ATAGCT |
| 256 | GCAAGA |
| 257 | GGAGAT |

TABLE 1-continued

| Seq. # | Sequence |
|---|---|
| 258 | TACAGC |
| 259 | CACTGA |
| 260 | ACAACC |
| 261 | ATGGTG |
| 262 | ATCTCA |
| 263 | ACGTTT |
| 264 | CCATAT |
| 265 | CAAGGT |
| 266 | AACCAC |
| 267 | CCATAG |
| 268 | ACACGA |
| 269 | GACGTA |
| 270 | CAGGAG |
| 271 | CACACA |
| 272 | AGTGTT |
| 273 | ATGCAG |
| 274 | AGCGAA |
| 275 | CACGTA |
| 276 | TACTGC |
| 277 | GCACAA |
| 278 | GAGGTA |
| 279 | TAGTGC |
| 280 | ACAGGA |
| 281 | ACCTAT |
| 282 | AGCTTG |
| 283 | ACGAGT |
| 284 | CACAGG |
| 285 | ACGTGA |
| 286 | ACCTAG |
| 287 | CGCAAC |
| 288 | TCCATA |
| 289 | AACGCG |
| 290 | AAGTCC |
| 291 | GAAGGC |
| 292 | CCGAAC |
| 293 | GACTGT |
| 294 | ACCGAA |
| 295 | ATCCTA |
| 296 | ACCATT |

TABLE 1-continued

| Seq. # | Sequence |
|---|---|
| 297 | CGACGA |
| 298 | CGAGTC |
| 299 | GGCAAT |
| 300 | GGGATG |
| 301 | GCATGA |
| 302 | CAACCT |
| 303 | AAGCGT |
| 304 | TGCAGA |
| 305 | AAGCGG |
| 306 | CCGATA |
| 307 | AGTACC |
| 308 | AGCAGA |
| 309 | GCAGAG |
| 310 | CTAGCA |
| 311 | CCAGAT |
| 312 | GCACTA |
| 313 | GACAGC |
| 314 | TACCGA |
| 315 | ACATCC |
| 316 | CGGTTG |
| 317 | CCATGA |
| 318 | GCAGTA |
| 319 | GCTTGA |
| 320 | CACAGC |
| 321 | GACCTA |
| 322 | GCACAG |
| 323 | ACAGCA |
| 324 | ACAGCG |
| 325 | AACCGT |
| 326 | ACTGGT |
| 327 | ACGCAG |
| 328 | AACCGG |
| 329 | AGCGTA |
| 330 | ATAGCC |
| 331 | AGGGTG |
| 332 | AGACCG |
| 333 | ACAGCT |
| 334 | CACTGC |
| 335 | CCAGTA |

TABLE 1-continued

| Seq. # | Sequence |
|---|---|
| 336 | TCAGCA |
| 337 | ACCTGA |
| 338 | GACCAC |
| 339 | GCCTAA |
| 340 | CCGTAG |
| 341 | CAGTGC |
| 342 | ATGCGT |
| 343 | CCACTG |
| 344 | CCAGTG |
| 345 | AGCTGT |
| 346 | CCCTAA |
| 347 | ACCGTA |
| 348 | GCGTTG |
| 349 | ACCACG |
| 350 | AGCGTT |
| 351 | ACCACT |
| 352 | CCCAAT |
| 353 | CCCAAC |
| 354 | GAGGGT |
| 355 | ACGCGA |
| 356 | ACCTCA |
| 357 | AGCAGC |
| 358 | CACCGA |
| 359 | GCCTAG |
| 360 | CCCATA |
| 361 | AGCCTA |
| 362 | GCCTAT |
| 363 | CAGCGT |
| 364 | GCCGAA |
| 365 | CGACCT |
| 366 | ACGTCC |
| 367 | CCGTGA |
| 368 | ACGGCA |
| 369 | ACAGCC |
| 370 | CCCTAC |
| 371 | ACCCTA |
| 372 | ACGGCT |
| 373 | GCGCAG |
| 374 | CCAGCA |

TABLE 1-continued

| Seq. # | Sequence |
|---|---|
| 375 | GCCTGA |
| 376 | ACCGGT |
| 377 | CAGCCT |
| 378 | GGCAGC |
| 379 | GGCCTA |
| 380 | TAAAAG |
| 381 | TAAAAT |
| 382 | TAAATC |
| 383 | TAATAG |
| 384 | TATAAT |
| 385 | TATTAA |
| 386 | GAAATA |
| 387 | TAAAGA |
| 388 | TAATAC |
| 389 | TAGAAA |
| 390 | TATAAC |
| 391 | TAACAA |
| 392 | TGAAAG |
| 393 | TTGAAA |
| 394 | TAAACT |
| 395 | TATATG |
| 396 | GTAAAT |
| 397 | TATTAT |
| 398 | TTATAT |
| 399 | GATAAT |
| 400 | TAAGAT |
| 401 | TAGAAG |
| 402 | TTATTA |
| 403 | GGAAAA |
| 404 | TTAGAA |
| 405 | TTATAC |
| 406 | GAAGAA |
| 407 | GATAAC |
| 408 | TAAGAC |
| 409 | TACTAA |
| 410 | TAACAG |
| 411 | TAACAT |
| 412 | TAAGTA |
| 413 | TACAAG |

TABLE 1-continued

| Seq. # | Sequence |
|---|---|
| 414 | TACAAT |
| 415 | TGAATG |
| 416 | CGAAAT |
| 417 | GATATA |
| 418 | TTAACA |
| 419 | TTTATT |
| 420 | GAAACA |
| 421 | TAAAGC |
| 422 | GAAACG |
| 423 | TAAGTG |
| 424 | TAATGG |
| 425 | TAATGT |
| 426 | GTTAAG |
| 427 | GTTAAT |
| 428 | TACATA |
| 429 | TATACA |
| 430 | TGTTAA |
| 431 | TTAAGG |
| 432 | TTGTAA |
| 433 | TTTATC |
| 434 | GAAAGG |
| 435 | GATATT |
| 436 | GCAAAA |
| 437 | GTTTAA |
| 438 | TATTGA |
| 439 | TTTTTG |
| 440 | ATTCAA |
| 441 | GAAGAT |
| 442 | GAGAAG |
| 443 | GATGAA |
| 444 | GTTAAC |
| 445 | TATACT |
| 446 | TCTAAC |
| 447 | TTTAGA |
| 448 | GTAATC |
| 449 | TACATG |
| 450 | TATAGT |
| 451 | TATGTA |
| 452 | TTACTA |

TABLE 1-continued

| Seq. # | Sequence |
|---|---|
| 453 | TTACAT |
| 454 | TTGATG |
| 455 | ATTACG |
| 456 | ATTTGA |
| 457 | CTTTAG |
| 458 | GAACAG |
| 459 | GAACAT |
| 460 | GAAGTA |
| 461 | GACAAT |
| 462 | GAGTAA |
| 463 | GTAGAA |
| 464 | TATCAG |
| 465 | TATCAT |
| 466 | ATATCG |
| 467 | CTAACG |
| 468 | GATAGA |
| 469 | TATTCA |
| 470 | TCATTA |
| 471 | TTATCA |
| 472 | CGTAAG |
| 473 | GAAAGC |
| 474 | GAACTG |
| 475 | GAATCA |
| 476 | GACAAC |
| 477 | GCTAAA |
| 478 | TACATC |
| 479 | TACTTT |
| 480 | TATCAC |
| 481 | TATGTT |
| 482 | TCATAC |
| 483 | TTGTAT |
| 484 | CGAATC |
| 485 | CGATAG |
| 486 | GAACTT |
| 487 | GAATGT |
| 488 | GCAAAG |
| 489 | TATCTT |
| 490 | TCTATT |
| 491 | TCTTAG |

TABLE 1-continued

| Seq. # | Sequence |
|---|---|
| 492 | TCTTAT |
| 493 | TGAAGG |
| 494 | TGGAAG |
| 495 | TGTTTA |
| 496 | TTCTAG |
| 497 | TTTAGG |
| 498 | GATTTC |
| 499 | TACAGA |
| 500 | TCTTTA |
| 501 | TTGGAA |
| 502 | TTGTAC |
| 503 | CGATAC |
| 504 | GCAAAC |
| 505 | TATGTC |
| 506 | TCATTT |
| 507 | TGTATC |
| 508 | TTTCAT |
| 509 | ATTTCG |
| 510 | CATACG |
| 511 | CTAGAC |
| 512 | TATCTC |
| 513 | TCGTAA |
| 514 | TGTTTG |
| 515 | TTTGTG |
| 516 | GTAGAT |
| 517 | GTGATA |
| 518 | TAAGCA |
| 519 | TAGCAA |
| 520 | TAGGAT |
| 521 | TAGTGA |
| 522 | TATGGA |
| 523 | TCGATA |
| 524 | TTTTGG |
| 525 | TTTTGT |
| 526 | CGACAA |
| 527 | GAGTTA |
| 528 | GTTTTT |
| 529 | CGTATG |
| 530 | GATCAT |

TABLE 1-continued

| Seq. # | Sequence |
|---|---|
| 531 | GCTAAT |
| 532 | GGAGAA |
| 533 | TAAGCT |
| 534 | TACACT |
| 535 | TGCTAA |
| 536 | AAGGTT |
| 537 | ATCGAT |
| 538 | CGTATT |
| 539 | GATTCA |
| 540 | GCAATG |
| 541 | TACAGT |
| 542 | TGAGTG |
| 543 | TGCAAG |
| 544 | TGTGAG |
| 545 | TTTGTC |
| 546 | AGTACG |
| 547 | ATACGG |
| 548 | ATACGT |
| 549 | ATTCGA |
| 550 | CGATTC |
| 551 | CGCAAA |
| 552 | GATCAC |
| 553 | GTTTTC |
| 554 | TACTCA |
| 555 | TGGATT |
| 556 | TTGAGG |
| 557 | ACGTTA |
| 558 | AGTGAC |
| 559 | ATGGAC |
| 560 | CTTCTA |
| 561 | GATCTT |
| 562 | GGACAA |
| 563 | GTACAC |
| 564 | GTATCA |
| 565 | TAAGGC |
| 566 | TACTGT |
| 567 | TGTACT |
| 568 | TGTGAC |
| 569 | TTTGGA |

TABLE 1-continued

| Seq. # | Sequence |
|---|---|
| 570 | GTGTAT |
| 571 | TACTCT |
| 572 | TAGCTA |
| 573 | TAGGTG |
| 574 | TAGTGT |
| 575 | TCTACT |
| 576 | TGACTC |
| 577 | TGTAGG |
| 578 | TTGGAC |
| 579 | GATGTC |
| 580 | GTAGTT |
| 581 | GTCTAG |
| 582 | TATGCA |
| 583 | TCTAGG |
| 584 | CGAGTA |
| 585 | CTGTTT |
| 586 | GAAGGT |
| 587 | GAGACT |
| 588 | GAGTTC |
| 589 | GATCTC |
| 590 | GCATTA |
| 591 | GGAAGT |
| 592 | TCTCTA |
| 593 | TGGTAC |
| 594 | TGTCAG |
| 595 | GACACA |
| 596 | GAGCAA |
| 597 | GAGGAT |
| 598 | GCATAC |
| 599 | GGATGA |
| 600 | GTACTC |
| 601 | GTCATT |
| 602 | TCATCT |
| 603 | TGAGGA |
| 604 | TGATGC |
| 605 | TGCTAT |
| 606 | TTGTCA |
| 607 | AATCCG |
| 608 | ACGACA |

TABLE 1-continued

| Seq. # | Sequence |
|---|---|
| 609 | ACTTCT |
| 610 | CTGACG |
| 611 | GATTGC |
| 612 | GTAGTC |
| 613 | TAGACC |
| 614 | TAGGTC |
| 615 | TCTGTG |
| 616 | TGTCAC |
| 617 | TGTGTT |
| 618 | TTGAGC |
| 619 | TTGGTG |
| 620 | TTGTGG |
| 621 | CGTACA |
| 622 | GCATTG |
| 623 | GGTTTG |
| 624 | GTTTGG |
| 625 | TACCAG |
| 626 | TCTGTT |
| 627 | TCTTGT |
| 628 | TGTCTT |
| 629 | TGTTCT |
| 630 | TTACGC |
| 631 | TTGCAG |
| 632 | TTGCAT |
| 633 | TTGTCT |
| 634 | ATACCG |
| 635 | CCGAAT |
| 636 | CTCGAG |
| 637 | GGAGTA |
| 638 | GTATGC |
| 639 | GTCATC |
| 640 | TATGGC |
| 641 | TGGACA |
| 642 | TTCTCT |
| 643 | ATACCT |
| 644 | TACCTG |
| 645 | TGACGT |
| 646 | TGCTTG |
| 647 | TTAGGC |

TABLE 1-continued

| Seq. # | Sequence |
|---|---|
| 648 | TTGCTG |
| 649 | CGTAGT |
| 650 | CGTGTA |
| 651 | GGCTAA |
| 652 | GTGTTC |
| 653 | TGCATC |
| 654 | TTGACC |
| 655 | TTGCTT |
| 656 | AGTCGA |
| 657 | CGCATA |
| 658 | GACTCT |
| 659 | GAGTGT |
| 660 | GATGGG |
| 661 | GGTGAT |
| 662 | GTGGAT |
| 663 | TGGGAT |
| 664 | TGTGGA |
| 665 | GATGCA |
| 666 | GCAGAT |
| 667 | GTTGGA |
| 668 | TTGGGA |
| 669 | ATGCGA |
| 670 | GATGCG |
| 671 | GTCACA |
| 672 | GTTTGC |
| 673 | TCTACC |
| 674 | TGGGAC |
| 675 | ATCACC |
| 676 | GTCACG |
| 677 | GTCGTA |
| 678 | TAGTCC |
| 679 | GGAGTC |
| 680 | TGCACA |
| 681 | TTCCTG |
| 682 | GACCAG |
| 683 | GACCAT |
| 684 | GCGTAT |
| 685 | TATGCC |
| 686 | TCAGGT |

TABLE 1-continued

| Seq. # | Sequence |
|---|---|
| 687 | TGACCA |
| 688 | GTCGTG |
| 689 | GTGAGC |
| 690 | GTGCTA |
| 691 | GTGTGG |
| 692 | TCGGTG |
| 693 | TCGTGG |
| 694 | TGCACT |
| 695 | TGGTGT |
| 696 | CCTGAC |
| 697 | CTTGCT |
| 698 | GAAGCC |
| 699 | GCAGTG |
| 700 | GGTTGT |
| 701 | GTGCAT |
| 702 | GTGTCT |
| 703 | TGCAGG |
| 704 | TGCAGT |
| 705 | TGGCAT |
| 706 | TGGGTT |
| 707 | TGGTCT |
| 708 | TGTGCA |
| 709 | TTGGGT |
| 710 | ATGGCG |
| 711 | CGGAGT |
| 712 | GACCTT |
| 713 | GCATCT |
| 714 | GGTTCT |
| 715 | GTTGCA |
| 716 | TGCCAA |
| 717 | TGTGCG |
| 718 | CTCGGA |
| 719 | CTGGGA |
| 720 | GTGCAC |
| 721 | TTGCGG |
| 722 | GCTTGT |
| 723 | GGTGTC |
| 724 | GTGACC |
| 725 | GTGCTT |

TABLE 1-continued

| Seq. # | Sequence |
|---|---|
| 726 | GTTGCT |
| 727 | TGGACC |
| 728 | GCAGTC |
| 729 | GGTCGA |
| 730 | TAGCCA |
| 731 | TGTCGC |
| 732 | TGTGGC |
| 733 | GGAGCA |
| 734 | GTCCAT |
| 735 | GTTGGC |
| 736 | TCCAGT |
| 737 | ATCCGT |
| 738 | CGTCGT |
| 739 | CTAGCC |
| 740 | GATGCC |
| 741 | GCTCTC |
| 742 | CTGGGT |
| 743 | GCTCGA |
| 744 | GTCCTT |
| 745 | CTGGCG |
| 746 | TGCCTG |
| 747 | CTACCC |
| 748 | GCCTTG |
| 749 | GGGTGT |
| 750 | TACCCT |
| 751 | TTGCCT |
| 752 | GTCTCC |
| 753 | GTGGCA |
| 754 | TGCGGG |
| 755 | TGTGCC |
| 756 | GGTGCT |
| 757 | GTTGCC |
| 758 | TCTGCC |
| 759 | TGCGCA |
| 760 | CTCCGT |
| 761 | CTGCCA |
| 762 | CAGGCC |
| 763 | CTGGCC |
| 764 | GCCTGT |

TABLE 1-continued

| Seq. # | Sequence |
|---|---|
| 765 | GTGCCT |
| 766 | TACCCC |
| 767 | GCCTCT |
| 768 | GTCCCA |
| 769 | AATAAA |
| 770 | TATAAA |
| 771 | ATAAAG |
| 772 | CTAAAA |
| 773 | ATAAAC |
| 774 | TTATAA |
| 775 | ATAATG |
| 776 | CATAAA |
| 777 | CTAAAG |
| 778 | CTAAAT |
| 779 | AGAAAC |
| 780 | ATATTA |
| 781 | TTATAG |
| 782 | TATATT |
| 783 | TTTATA |
| 784 | CTATAA |
| 785 | AAGATA |
| 786 | GATAAG |
| 787 | CATAAG |
| 788 | TATTAC |
| 789 | ATATTG |
| 790 | ATTATG |
| 791 | ATGAAG |
| 792 | ATTTAT |
| 793 | ATGAAT |
| 794 | ATAACA |
| 795 | GTAATA |
| 796 | CTAATG |
| 797 | AATACA |
| 798 | TTGAAG |
| 799 | ATTTTA |
| 800 | TTACAA |
| 801 | AATTGA |
| 802 | AATACT |
| 803 | CATATA |

TABLE 1-continued

| Seq. # | Sequence |
|---|---|
| 804 | ATATTC |
| 805 | AGTAAT |
| 806 | ATTATC |
| 807 | TGTAAT |
| 808 | AATAGT |
| 809 | ATTTTG |
| 810 | AGAATC |
| 811 | TGATAT |
| 812 | AGTTAA |
| 813 | TATGAG |
| 814 | AGGAAA |
| 815 | AGTAAC |
| 816 | CTTATA |
| 817 | AGATTA |
| 818 | AATCAG |
| 819 | TAGATT |
| 820 | GATTAT |
| 821 | AGAAGA |
| 822 | ATAGAC |
| 823 | CATATT |
| 824 | CATTAG |
| 825 | ACTATA |
| 826 | CTCAAA |
| 827 | ATACAT |
| 828 | AGTATA |
| 829 | GTATAT |
| 830 | GTATAG |
| 831 | CAGAAT |
| 832 | CATGAA |
| 833 | TATAGG |
| 834 | TAGTAT |
| 835 | ATTGAG |
| 836 | ATTGAT |
| 837 | TGATTG |
| 838 | TTAGTA |
| 839 | ATGATT |
| 840 | CATTAC |
| 841 | GATATC |
| 842 | GTTATA |

TABLE 1-continued

| Seq. # | Sequence |
|---|---|
| 843 | CTGAAG |
| 844 | AGAACA |
| 845 | CTTTAT |
| 846 | CTATTT |
| 847 | ATCATA |
| 848 | CTACAA |
| 849 | ATAAGC |
| 850 | AAGACA |
| 851 | CATATC |
| 852 | ACTATG |
| 853 | ATATGT |
| 854 | ATAGTG |
| 855 | ATTGAC |
| 856 | AGTATG |
| 857 | TGTATG |
| 858 | ATATCT |
| 859 | AGTATT |
| 860 | ATTGTA |
| 861 | TTATGT |
| 862 | ATTAGG |
| 863 | CTAACT |
| 864 | GTTATG |
| 865 | CATAGA |
| 866 | TCTATG |
| 867 | AGCAAA |
| 868 | GTGAAG |
| 869 | TGCAAA |
| 870 | AGGAAT |
| 871 | TGTGAA |
| 872 | TTTGTA |
| 873 | GGAATG |
| 874 | AGATTC |
| 875 | TTCTAT |
| 876 | GTGAAT |
| 877 | ATGTAC |
| 878 | ATCTTA |
| 879 | AAGGAG |
| 880 | AAGAGG |
| 881 | TTTAGT |
| 882 | AGAGAT |
| 883 | ATCTAC |
| 884 | GAGATG |
| 885 | TTTCTA |
| 886 | CCTAAA |
| 887 | AATACC |
| 888 | CTCAAG |
| 889 | CGAAGA |
| 890 | CATTTC |
| 891 | CATGAG |
| 892 | ATTGTG |
| 893 | AGTATC |
| 894 | GATTGA |
| 895 | ATCTTG |
| 896 | AGAGAC |
| 897 | ATTTGT |
| 898 | AGGTAA |
| 899 | GTAAGG |
| 900 | GTAAGT |
| 901 | GTGTAA |
| 902 | ATGTTT |
| 903 | CAGATT |
| 904 | AAGGTA |
| 905 | GGTAAG |
| 906 | GATACT |
| 907 | AGTTTT |
| 908 | AGTAGA |
| 909 | CTACAG |
| 910 | GGTTAA |
| 911 | CATGAC |
| 912 | ACTCAA |
| 913 | AGGATA |
| 914 | GAGTAT |
| 915 | CTTGAG |
| 916 | CTTACA |
| 917 | TTATGC |
| 918 | AAGTCA |
| 919 | ACGATG |
| 920 | AGACTG |

TABLE 1-continued

| Seq. # | Sequence |
|---|---|
| 921 | ATGACT |
| 922 | ATTGTC |
| 923 | GTAGAC |
| 924 | CTAAGC |
| 925 | TTGACG |
| 926 | AAGGTG |
| 927 | TCTCAA |
| 928 | CAGATC |
| 929 | ACTACA |
| 930 | AAGCTA |
| 931 | ATCTTC |
| 932 | ATGAGG |
| 933 | GTGATG |
| 934 | AGATGT |
| 935 | AGTGAG |
| 936 | AGAGTG |
| 937 | AGCAAT |
| 938 | ATGCAA |
| 939 | GTACAT |
| 940 | CTACTT |
| 941 | CTATGT |
| 942 | CTATGG |
| 943 | CGAACT |
| 944 | CAGGAA |
| 945 | TGTGAT |
| 946 | CTTGAC |
| 947 | AGTACA |
| 948 | CAGTAC |
| 949 | GGTATA |
| 950 | CTTGTA |
| 951 | TTGTGA |
| 952 | CTCTAT |
| 953 | CTATCT |
| 954 | TTCGAG |
| 955 | CAGAGA |
| 956 | GATGTT |
| 957 | CATGTG |
| 958 | GTGATT |
| 959 | GATTGG |

TABLE 1-continued

| Seq. # | Sequence |
|---|---|
| 960 | CTTAGT |
| 961 | CCTAAG |
| 962 | CGTGAA |
| 963 | GTAAGC |
| 964 | CATCTG |
| 965 | AGTACT |
| 966 | CTTCAG |
| 967 | CTGAGA |
| 968 | GTATGT |
| 969 | TCGTAG |
| 970 | TTGGTA |
| 971 | GTTGTA |
| 972 | TTAGGG |
| 973 | GTTAGG |
| 974 | AGACGA |
| 975 | CTAGTC |
| 976 | CTGTTG |
| 977 | ATCAGG |
| 978 | ATGTCA |
| 979 | CGACAG |
| 980 | GTCTTA |
| 981 | CGTTTT |
| 982 | ACTGTG |
| 983 | AATGGC |
| 984 | ACGTTG |
| 985 | CTTTCT |
| 986 | CTCTTT |
| 987 | CTCATC |
| 988 | AGATGC |
| 989 | AGTGTG |
| 990 | CTAGGA |
| 991 | GTAACC |
| 992 | CTATGC |
| 993 | ATGTCG |
| 994 | ACTCTG |
| 995 | TGTGTG |
| 996 | ACTGTT |
| 997 | ACTCAC |
| 998 | TAGCAC |

TABLE 1-continued

| Seq. # | Sequence |
|---|---|
| 999 | ATCTGG |
| 1000 | TGTTGG |
| 1001 | AGTCTG |
| 1002 | TGTTGT |
| 1003 | TGGTTG |
| 1004 | GTTGTG |
| 1005 | ATTGGG |
| 1006 | CGAAGC |
| 1007 | TTGTCG |
| 1008 | ACTCTT |
| 1009 | ATTGGT |
| 1010 | TCGTTG |
| 1011 | GATACC |
| 1012 | ATTTCC |
| 1013 | AGCATT |
| 1014 | ATACCA |
| 1015 | CGATGG |
| 1016 | CGGATG |
| 1017 | CGATGT |
| 1018 | GTTTGT |
| 1019 | CATACC |
| 1020 | CCTATG |
| 1021 | ACTAGC |
| 1022 | CGTGAT |
| 1023 | ATGCTG |
| 1024 | CTGAGT |
| 1025 | ATAGGC |
| 1026 | CGATCT |
| 1027 | CGTTGA |
| 1028 | CTGTGA |
| 1029 | GTGACA |
| 1030 | GGTAGA |
| 1031 | GGGATA |
| 1032 | CTCTGA |
| 1033 | CCTGAA |
| 1034 | ATCAGC |
| 1035 | GTTGTC |
| 1036 | GTGACT |
| 1037 | AAGGGT |

TABLE 1-continued

| Seq. # | Sequence |
|---|---|
| 1038 | ACTCGA |
| 1039 | AGAGGT |
| 1040 | AGGAGT |
| 1041 | CTGGTA |
| 1042 | AGGGAT |
| 1043 | ATGTGC |
| 1044 | GTGTGA |
| 1045 | GTGCAA |
| 1046 | CTAGGG |
| 1047 | CTAGGT |
| 1048 | TGGTGA |
| 1049 | GAGGTG |
| 1050 | GGTACA |
| 1051 | CCTATC |
| 1052 | TGTTGC |
| 1053 | ATGCTC |
| 1054 | TTGTGC |
| 1055 | AGTTGC |
| 1056 | CGTCAT |
| 1057 | TCTGGA |
| 1058 | CCTTTG |
| 1059 | AAGGCG |
| 1060 | GGTGAC |
| 1061 | AGCGAT |
| 1062 | CAGCAG |
| 1063 | CAGCAT |
| 1064 | CAGTCT |
| 1065 | CCTAGA |
| 1066 | CGTGTG |
| 1067 | AGCTGA |
| 1068 | CTGTGT |
| 1069 | CTGTCG |
| 1070 | CGTTGG |
| 1071 | CGTTGT |
| 1072 | CGCATG |
| 1073 | CCTCAA |
| 1074 | TAGGGG |
| 1075 | GCTACA |
| 1076 | CTCTGT |

TABLE 1-continued

| Seq. # | Sequence |
|---|---|
| 1077 | GTAGCA |
| 1078 | CTTCGT |
| 1079 | CAGCAC |
| 1080 | CATGCT |
| 1081 | ACGGTG |
| 1082 | CCGATG |
| 1083 | CTTGCA |
| 1084 | AGACCA |
| 1085 | GTGTCA |
| 1086 | AGCACG |
| 1087 | AGGTGG |
| 1088 | GGATGC |
| 1089 | TGTCGT |
| 1090 | GATGGC |
| 1091 | CCTTGA |
| 1092 | AGGCTA |
| 1093 | AGTCGT |
| 1094 | AGGCAG |
| 1095 | GTCTGG |
| 1096 | AGCAGT |
| 1097 | AGTGCA |
| 1098 | TGACCT |
| 1099 | CGTCTC |
| 1100 | AGGTCT |
| 1101 | AGGGTT |
| 1102 | GGTGTT |
| 1103 | AAGCGC |
| 1104 | GTACCA |
| 1105 | CGGTGA |
| 1106 | AGCGTG |
| 1107 | ATGCGG |
| 1108 | CGGCAA |
| 1109 | CCTAGT |
| 1110 | CTGTGC |
| 1111 | ATTGCC |
| 1112 | CGCAGA |
| 1113 | CGAGCA |
| 1114 | CGTTGC |
| 1115 | CTCCAT |
| 1116 | GTACCT |
| 1117 | CATCCT |
| 1118 | CCTCAT |
| 1119 | AAGCCT |
| 1120 | GCGTTT |
| 1121 | CCGTTG |
| 1122 | GCGACA |
| 1123 | AGGTGC |
| 1124 | GTGTGC |
| 1125 | AGTCGC |
| 1126 | ACTCCA |
| 1127 | AGTCCA |
| 1128 | CGGTCA |
| 1129 | CAGGGG |
| 1130 | AAGGCC |
| 1131 | GGTTGC |
| 1132 | GGTACC |
| 1133 | TGCCTA |
| 1134 | CTCGGT |
| 1135 | TTGCCA |
| 1136 | AGCCTG |
| 1137 | AGCACC |
| 1138 | GGACCA |
| 1139 | ATGCCT |
| 1140 | CGCTGT |
| 1141 | TAGGCC |
| 1142 | AGGTCC |
| 1143 | CCTTGC |
| 1144 | GGCAGT |
| 1145 | GGTGCA |
| 1146 | AGTGCC |
| 1147 | AGCTCC |
| 1148 | AGCCTC |
| 1149 | AGCGCA |
| 1150 | GAGCCT |
| 1151 | CCGGTT |
| 1152 | AGTCC |

Oligonucleotides of the present invention may comprise sequences in addition to the hybridization sequence of length n. In many cases, the additional sequences are positioned 5' of the hybridization sequence. The additional sequence may be, for example, a promoter recognition sequence. In a preferred embodiment, the promoter recognition sequence is a bacteriophage promoter recognition sequence, such as a T7 or a T3 promoter recognition sequence. In certain aspects of the invention, the additional sequence may be an adapter or linker sequence for cloning manipulations. For example, the additional sequence may be a restriction enzyme recognition sequence.

In certain aspects of the invention, the oligonucleotide further comprises a spacer sequence positioned between the hybridization sequence of length n and the promoter recognition sequence.

In certain aspects of the invention, the oligonucleotide primer may be labeled and/or a label may be incorporated into a sequence transcribed from the oligonucleotide primer. Labeling facilitates the detection of the molecules in applications such as expression analysis. A number of different labels may be used in the present invention such as fluorophores, chromophores, radiophores, enzymatic tags, antibodies, chemiluminescence, electroluminescence, and affinity labels. Those of skill in the art are familiar with methods for labeling nucleic acids and will recognize that these and other labels not mentioned herein can be used with success in this invention.

Examples of affinity labels include, but are not limited to the following: an antibody, an antibody fragment, a receptor protein, a hormone, biotin, DNP, or any polypeptide/protein molecule that binds to an affinity label.

Examples of enzyme tags include enzymes such as urease, alkaline phosphatase or peroxidase to mention a few. Colorimetric indicator substrates can be employed to provide a detection means visible to the human eye or spectrophotometrically, to identify specific hybridization with complementary nucleic acid-containing samples. All of these examples are generally known in the art and the skilled artisan will recognize that the invention is not limited to the examples described above.

Examples of fluorophores include, but are not limited to the following: Alexa 350, Alexa 430, AMCA, BODIPY 630/650, BODIPY 650/665, BODIPY-FL, BODIPY-R6G, BODIPY-TMR, BODIPY-TRX, Cascade Blue, Cy2, Cy3, Cy 3.5, Cy5, Cy5.5, Cy7, 6-FAM, Fluoroscein, HEX, 6-JOE, Oregon Green 488, Oregon Green 500, Oregon Green 514, Pacific Blue, REG, Rhodamine Green, Rhodamine Red, ROX, TAMRA, TET, Tetramethylrhodamine, lissamine, phycoerythrin, FluorX, and Texas Red.

In one embodiment, the present invention provides a kit in suitable container means comprising a plurality of oligonucleotide primers comprising between 50-2,500 non-identical template hybridization sequences of 4, 5, 6, 7, 8, 9, 10, or 11 nucleotides in length. In some embodiments, the kit comprises between about 100 to 2500, 100 to 2000, 100 to 1500, 300 to 1500, or any range therein of oligonucleotide primers having non-identical hybridization sequences. In a preferred embodiment, the oligonucleotide primers of the kit comprise Sequence #s 1 to 379. In another preferred embodiment, the oligonucleotide primers of the kit comprise Sequence #s 1 to 1152. In certain aspects of the invention, the plurality of oligonucleotide primers further comprise a promoter recognition sequence. In some aspects of the invention, the plurality of oligonucleotide primers further comprise a label. In some embodiments, the kit further comprises one or more of an oligo-d(T) primer; a reverse transcriptase; a buffer; a dNTP mix; an RNA polymerase; a single strand binding protein; ethylenediaminetetraacetic acid (EDTA); a promoter-oligo-d(T) primer; a ribonuclease inhibitor; a DNA polymerase; RNase H; nuclease free water; ATP; CTP; GTP; UTP; TTP; DNase I; an aRNA filter cartridge; a cDNA filter cartridge; or collection tubes.

In one embodiment, the invention provides a computer readable medium comprising computer executable instructions, the instructions comprising: identifying an exclusion sequence; comparing oligonucleotides having hybridization sequences of length n to the exclusion sequence to identify particular hybridization sequences of length n that are expected to substantially hybridize to the exclusion sequence, the exclusion sequence and the identified particular hybridization sequences of length n defining an exclusion set; and identifying a plurality of oligonucleotides having non-identical hybridization sequences of length n that are not within the exclusion set.

In certain aspects of the invention, the computer executable instructions for comparing hybridization sequences of length n to the exclusion sequence comprise one or more of the following: identifying a set of all possible sequences of length n; identifying a set of all sequences of length n contained in the exclusion sequence; comparing the set of sequences of length n contained in the exclusion sequence to the set of all possible sequences of length n; excluding from the pool of oligonucleotides those oligonucleotides having at their 3' end a sequence of length n that is identical to a sequence of length n contained in the exclusion sequence; retaining in the pool of oligonucleotides those oligonucleotides having at their 3' end a sequence of length n that has at least 2 mismatches when compared to the set of all sequences of length n contained in the exclusion sequence; assessing binding free energy ($\Delta G$) of the oligonucleotides and excluding from the pool of oligonucleotides those oligonucleotides having low $\Delta G$; and/or excluding from the pool of oligonucleotides those oligonucleotides in which the only mismatch is a GU at the 5' end of the sequence of length n.

It is contemplated that any method or composition described herein can be implemented with respect to any other method or composition described herein.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

This figure illustrates a primer design protocol for selecting a pool of 6-mer oligonucleotides that are not expected to hybridize to rRNA sequences.

Figure 2A:
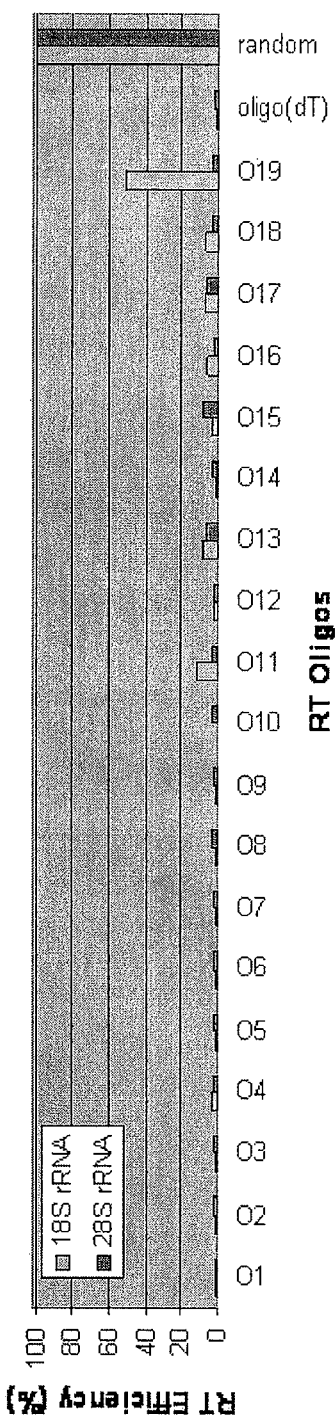
Figure 2B:
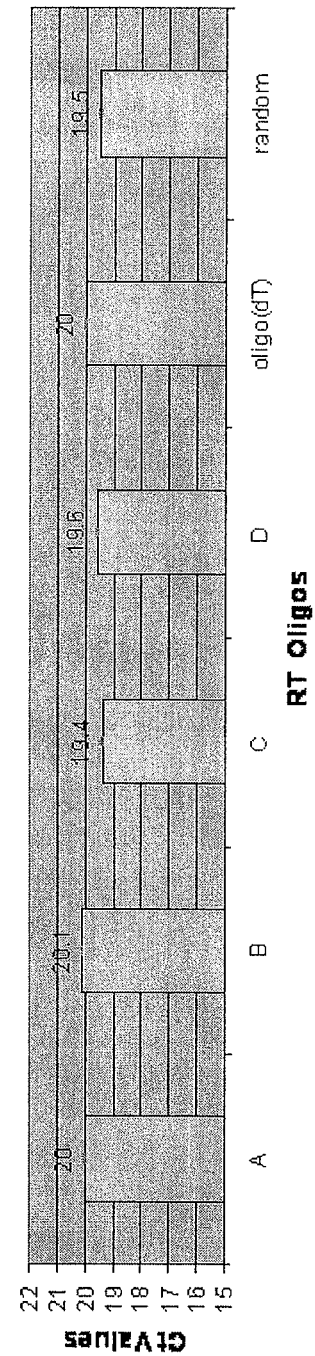

FIGS. 2A and 2B. GAPDH cDNA Synthesis Using Gene Specific 6-mer RT Primers.

RT and real-time PCR experiments were performed to test 19 GAPDH specific 6-mer oligos. FIG. 1A illustrates the RT efficiency of individual 6-mer oligos for 18S and 28S rRNAs. RT efficiency was calculated as a percentage of cDNA yield using random hexamer RT primers. The rRNA-derived cDNA yield for each RT reaction was evaluated by real-time PCR with gene specific primers for 18S or 28S rRNA. As can be seen in FIG. 1A, the GAPDH specific 6-mer oligos do not efficiently prime the reverse transcription of 18S and 28S rRNA. The 6-mer oligos were grouped according to their RT efficiency for rRNA. Group A in FIG. 2B contains 10 oligos with the lowest RT efficiency for rRNA (O1, O2, O3, O5, O6, O7, O8, O9, O10, O12, and O14); Group B contains Group A+O4+O13+O15; Group C contains Group B+O16+O17+O18; Group D contains Group C+O11+O19. These oligo groups were used as RT primers in separate reactions, and the GAPDH cDNA synthesis efficiency of the different primer groups were compared by real-time PCR. As illustrated in FIG. 2B, Groups A, B, C, and D exhibited RT efficiency for GAPDH similar to that of oligo-d(T) primers and random hexamer primers.

Figure 3:
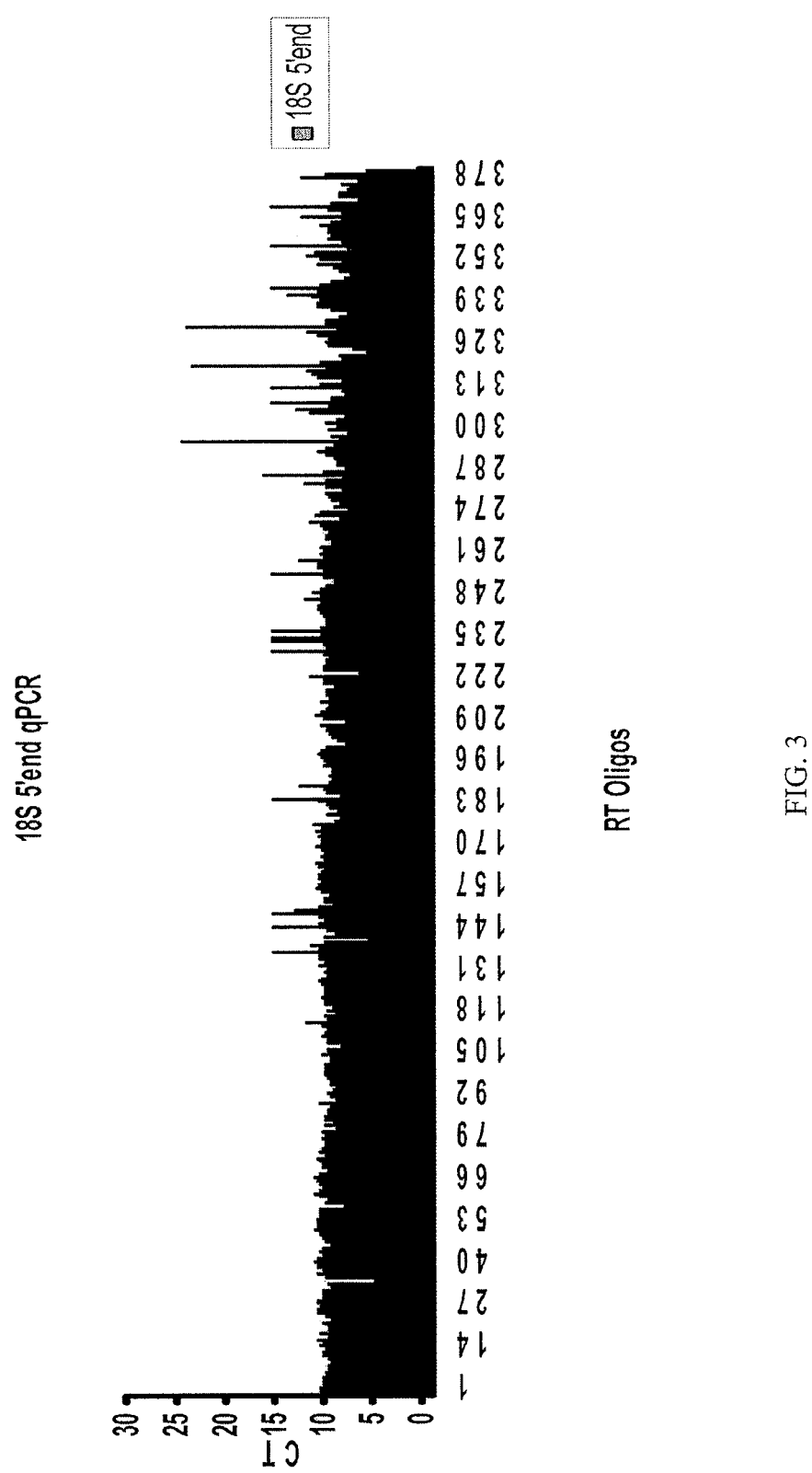

FIG. 3. The RT Selectivity of 379 Individual Oligonucleotides Against 18S rRNA.

Each of Sequence #s 1 to 379 were tested individually for their RT selectivity against 18S rRNA. The selectivity was determined by real-time PCR.

Figure 4:
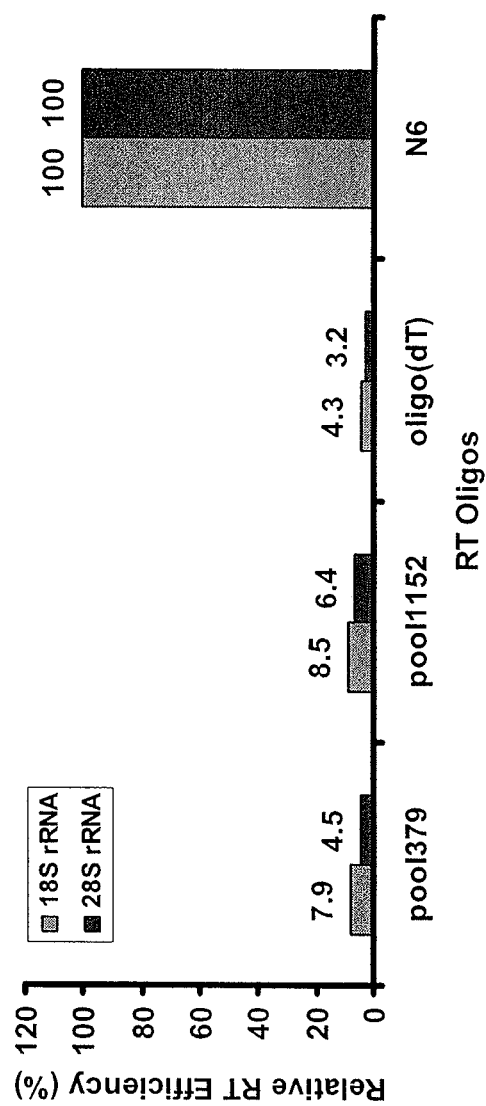

FIG. 4. The RT Efficiency of Two Oligonucleotide Pools for rRNA.

RT efficiency for 18S and 28S rRNAs with RT primer pools of Sequence #s 1-379 (pool379 in FIG. 4) and Sequence #s 1-1152 (pool1152 in FIG. 4) was evaluated. RT reaction with random hexamers was used as the baseline (100% RT efficiency) and was compared to reactions using pool379, pool1152, and oligo-d(T) primers. The RT efficiency was determined real-time PCR assays (Ct values). As shown in FIG. 4, both pool379 and pool1152 had low RT efficiency for rRNA.

Figure 5:
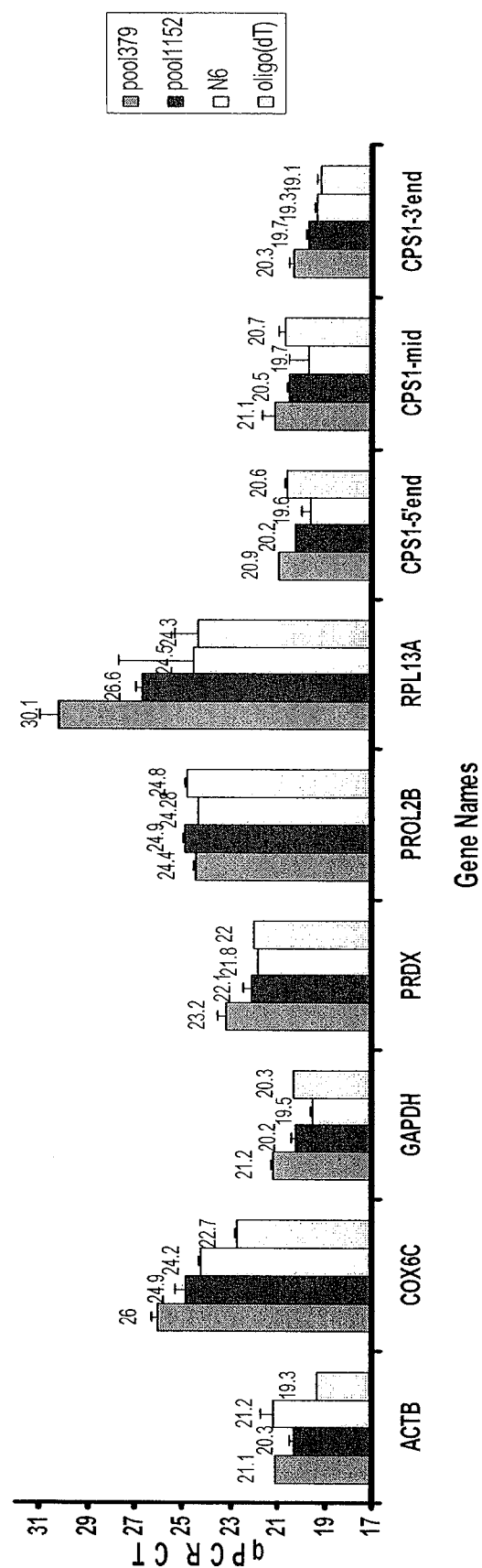

FIG. 5. RT Efficiency for mRNA.

The RT efficiency for GAPDH, ACTB, COX6C, CPS1, JUN, IL-18, POLR2B, and RPL13A mRNA with RT primer pools of Sequence #s 1-379 (pool379 in FIG. 5) and Sequence #s 1-1152 (pool1152 in FIG. 5) was evaluated. The RT efficiency was determined using real-time PCR assays (Ct values). For CPS1, three PCR tests using primer pairs from different regions of the gene sequence were performed.

FIGS. 6A and 6B. Eberwine Amplification.

FIG. 6A illustrates the conventional Eberwine RNA amplification using oligo-d(T) primers. FIG. 6B illustrates a modified Eberwine RNA amplification using an in silico designed primer set.

FIGS. 7A, 7B, 7C, and 7D.

Figures 7A, 7B, 7C, 7D:
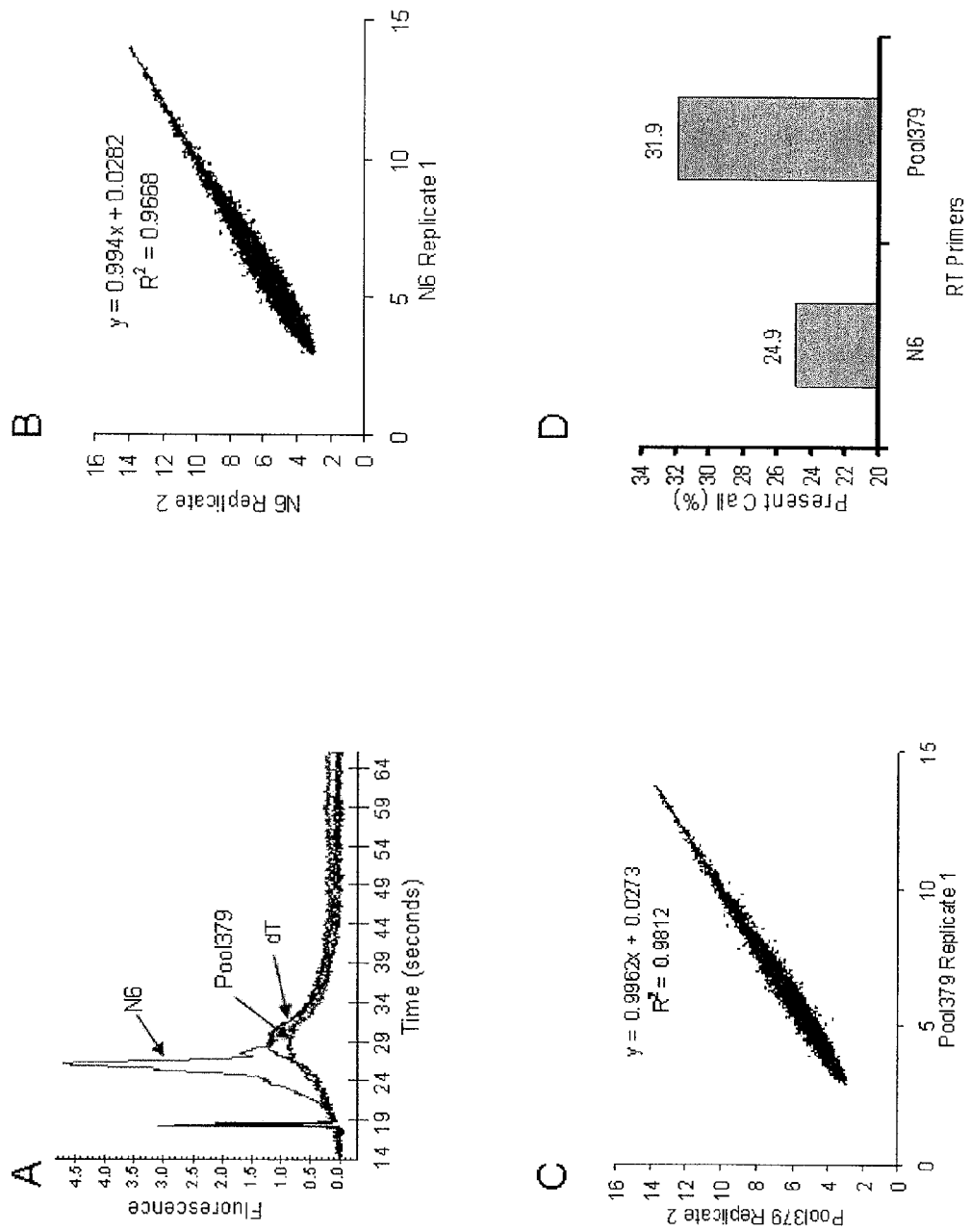

Primer evaluations by Affymetrix arrays. Random hexamers or Pool379 were used as primers in RT reactions. T7 amplified total RNA were applied to microarrays and the percent of Present Calls were determined using MASS package from Affymetrix. The percentages of Present Calls were averaged within each group (Pool379 RT or N6 RT). FIG. 7A: Total RNA linear amplification with T7 tagged primers (random hexamers, oligo dT or Pool379). FIG. 7B: Signal correlation between two technical replicates with random hexamers as RT primers. FIG. 7C: Signal correlation between two technical replicates with Pool379 as RT primers. FIG. 7D: Average Percentage of Present Calls on Affymetrix arrays.

FIG. 8.

Figure 8:
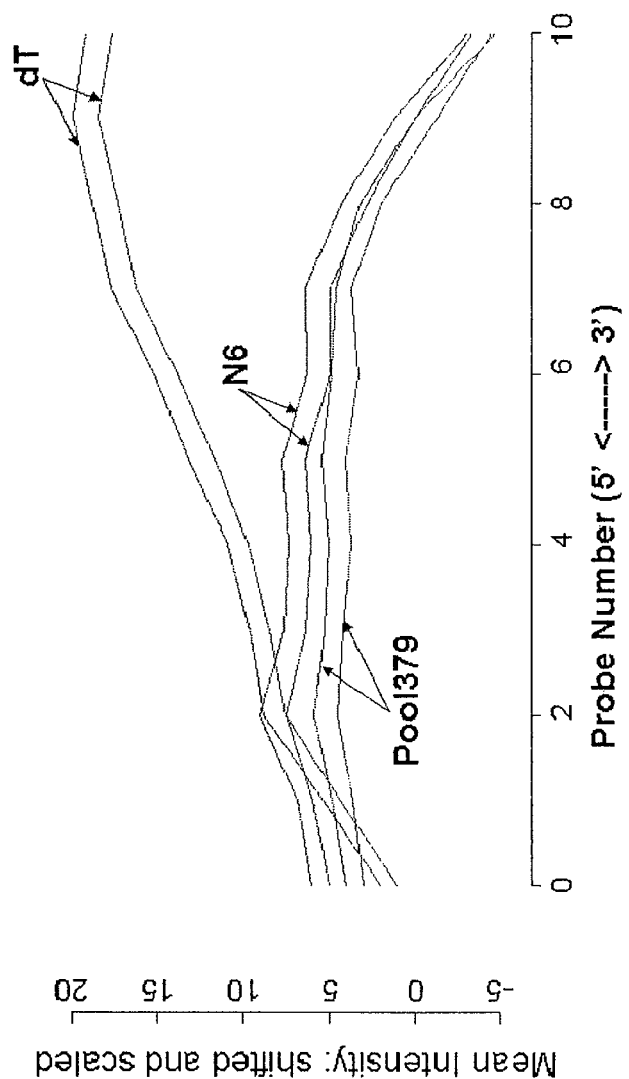

Random hexamers or Pool379 were used as primers in RT reactions. T7 amplified total RNA were applied to microarrays. Plots were generated using the BioConductor package and were used to describe the tendency of 5' to 3' bias of Affymetrix arrays. As shown in FIG. 8, the oligo dT was biased toward 3' probes whereas N6 and Pool379 were not. N6 and Pool379 showed a bias against the very 3' end.

DESCRIPTION OF ILLUSTRATIVE EMBODIMENTS

A. Computational Oligonucleotide Design

The present invention provides novel algorithms for designing oligonucleotides that do not substantially hybridize to a small group of unwanted transcripts, while hybridizing to most other transcripts. Such oligonucleotides are particularly useful as primers for reverse transcription. A computational selection method may be used to select or design primers in silico. A computational selection method may employ, for example, an algorithm having one or more selection filters to select or design the desired oligonucleotides.

One consideration in the computational design of oligonucleotide primers is the length of the hybridization sequence. Oligonucleotides of any length can be designed using the methods of the present invention. It should be taken in to consideration, however, that the average number of binding sites per oligo decreases dramatically as the oligo length increases. As a result, as the length of the random oligos increases more oligos are needed for whole transcriptome coverage. On the other hand shorter oligos may result in less RT efficiency and less selectivity against unwanted sequences. Table 2 shows the average number of binding sites in the human transcriptome for oligonucleotides of various lengths.

TABLE 2

| | Oligo Length | | | | |
|---|---|---|---|---|---|
| | 6 | 7 | 8 | 9 | 10 |
| Average Binding Sites per Oligo* | 18,554 | 4,638 | 1,159 | 290 | 72 |

*The number of average binding sites were calculated based on the human RefSeq dataset downloaded on Apr. 20, 2005, which contained $7.6 \times 10^7$ nucleotides from 29,176 sequences.

Another consideration in the computational design of oligonucleotide primers is the sequence of the exclusion sequence or sequences. The exclusion sequence can be any sequence to which hybridization of the oligonucleotides is not desired. It may be desirable to exclude, for example, certain abundant transcripts such as rRNAs and highly expressed mRNAs. As described in more detail in the Examples section below, a pool of oligonucleotide primers that do not anneal to rRNA sequences but provide specific and sufficient coverage for most other RNAs were designed by computational prediction.

The following description of the computational selection of a pool of 6-mer oligonucleotide primers that selectively and efficiently reverse transcribe most RNAs but do not substantially reverse transcribe human rRNAs is illustrative of a computational design approach according to the present invention. Those of skill in the art would be able to modify this method for use with other exclusion sequences and to design oligonucleotide primers of any desired length.

The combined sequences of 28S, 18S, and 5.8S human rRNA have 7,063 nucleotides (GenBank accession number #U13369). The human 28S, 18S, and 5.8S rRNA sequences were downloaded from GenBank, parsed into 6-mers, and screened against all possible 6-mer sequences (4,096 total). A series of filters were applied to discriminate against those 6-mer sequences that were likely to anneal to the rRNA sequences. These filters are summarized below:

An oligo was rejected if it was found in rRNA sequences.
An oligo was retained if it had at least 2 mismatches when compared to all rRNA 6-mer sequences.
An oligo was retained if it has a single mismatch to rRNAs and this mismatch is not a GU wobble pair.
An oligo was retained if its only mismatch to rRNAs was a GU mismatch that was not at the 5' terminus of the oligo.
If the only mismatch was a GU wobble pair at the 5' end, then hits to rRNAs and perfect matches to mRNAs were considered. If the hits to rRNAs were greater than 3 or the matches to mRNAs were less than 3000, then the oligo was rejected. The hits to rRNAs were defined as the number of 3' five-base matches to the rRNA sequences. The hits to mRNAs were defined as the number of occurrences of oligos perfectly matched to an mRNA sequence. Each mRNA was counted only once.
An oligo was rejected if its binding free energy ($\Delta G$) was below −8 kcal/mol.

$\Delta G$ values were used as a filter because a primer with low primer-RNA duplex stability (as measured by Gibbs free energy ($\Delta G$)) increases the likelihood that the primer will cross-hybridize to rRNA. The GU wobble filter was used because a GU wobble pair can still contribute significantly to thermodynamic stability, although less than standard GC Watson-Crick pairs (Kierzek et al., 1999). Thus, a GU wobble pair mismatch may not be enough to prevent priming to rRNAs. Nucleotides at the 3' end region of an oligo are important for primer extension by reverse transcriptase (Ayyadevara et al., 2000; Huang et al., 1992); therefore, a GU mismatch in this region may be sufficient in deterring reverse transcription of rRNAs. Contiguous base matching can stabilize an annealing nucleic acid duplex (Willems et al., 1989; Hughes et al., 2001); thus a 5' terminal GU wobble pair may not be sufficient in preventing mispriming to rRNAs. In determining whether to retain or reject an oligo in which the only mismatch to rRNAs is a GU wobble pair at the 5' end, one may also want to consider and balance mRNA coverage and selectivity against rRNAs. For example, if such an oligo has very few hits to rRNAs (e.g., less than 3) and/or has many hits to mRNA (e.g., greater than 3000), it may be desirable to retain the oligo.

Figure 1:
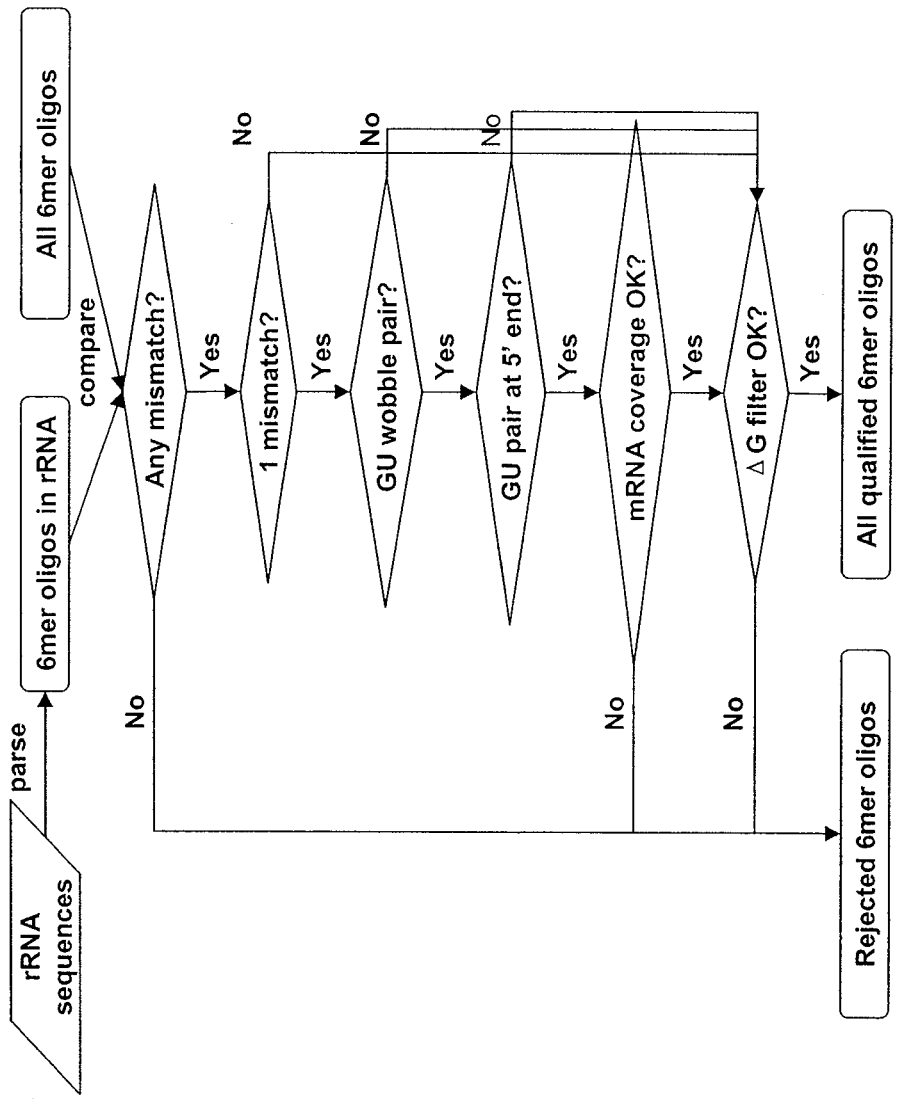
FIG. 1. Algorithm For Reverse Transcription Primer Design.

A flowchart of the computation primer design protocol is provided in FIG. 1. It should be noted, however, that the filters listed above and shown in FIG. 1 do not have to be performed in any particular order. It should also be noted that not all filters have to be used to design the oligonucleotides.

Among all possible 4096 6-mer oligos, 1152 passed all of the screening filters described above. The sequences of the 1152 6-mer oligonucleotides are provided in Table 1. On average, this set of 1152 primers provides 686 binding sites for one transcript. Because of the high coverage, it is possible to apply more stringent filters to further increase selectivity against rRNAs while maintaining sufficient mRNA coverage. A smaller pool with 379 oligos was obtained after excluding oligos with only a single GU wobble pair mismatch to rRNAs. This smaller pool (sequences 1 to 379 in Table 1) provides 213 binding sites per mRNA transcript on average. Both sets of primers are expected to provide thorough coverage of the transcriptome. The number of binding sites was calculated based on the human RefSeq dataset of 29,176 sequences.

This primer set can also be applied to mouse and rat RT reactions because of the very high sequence homology between human rRNAs, mouse rRNAs (NCBI Accession # BK000964), and rat rRNAs (NCBI Accession # V01270). Of the 1152 6-mer oligonucleotides selected, 1090 of them were predicted to be selective against mouse rRNAs and 1075 against rat rRNAs. Therefore, this oligo pool can be used for rRNA reduction in RT for either human, mouse or rat transcriptome.

B. RNA

There are several types of naturally occurring RNA molecules including messenger RNA (mRNA), transfer RNA (tRNA), ribosomal RNA (rRNA), microRNA, and siRNA. The "transcriptome" refers to the complete collection of transcribed elements of the genome. These molecules perform many different functions in the cell. mRNA, which conveys information from the nucleus to the cytoplasm in eukaryotes, is the most intensely studied. Several molecular biology procedures use purified mRNA as starting material or are designed to work primarily with mRNA. These procedures include: cDNA synthesis (for library construction, RT-PCR analysis, or 5' end analysis through primer extension); Northern blot analysis; ribonuclease protection assays; screening procedures involving in vitro translation; and gene expression analysis with microarrays.

There are several existing procedures to purify RNA from various biological samples. However, mRNA represents only 1-5% of the mass of total RNA (Sambrook, 2001). Of the remainder, the major RNA species is ribosomal RNA (rRNA), constituting 80% or more of total RNA mass (Sambrook et al., 1989 and 2001). Although the total RNA isolated from cells can sometimes be used for the above-mentioned procedures, usually a preliminary purification of mRNA from total RNA is often preferred, if not required. This is especially true if the particular mRNA being sought or targeted is in low abundance (0.5% or less of the mRNA population). The presence of rRNA can interfere in the detection of mRNA by Northern blotting, RNase protection assays, differential display analysis, and expression profiling by gene arrays, especially if the target being analyzed is in low abundance. Often, the mRNA from scientifically interesting genes falls into this category. Abundant mRNA transcripts can also interfere with the analysis of less abundant mRNA species. For example, globin mRNA constitutes 70% of total mRNA isolated from whole blood. The presence of globin mRNA can significantly affect expression analysis of other genes in blood transcriptional studies.

As the first step in expression analysis, RNAs of interest are usually converted to cDNA. This conversion is performed with a reverse transcription (RT) reaction. Currently two types of oligonucleotides primers, oligo dT and random hexamers are commonly used to anneal to RNA molecules to start the RT reactions. Unfortunately, both priming methods have major limitations.

Random primers are commonly used in RT reactions for total RNA. Typically, most of the RNA in a sample is rRNA, whereas other transcripts (e.g. mRNAs) comprise only a small percentage of total RNA. As a result, the overwhelming majority of final cDNA products will be from rRNAs. The presence of these rRNA-derived products may be detrimental to many downstream applications such as microarrays. Removing rRNA prior to microarray hybridization results in a higher percentage of present calls, which is an indication of better array sensitivity. rRNA removal also results in increased sample correlations/concordance among array replicates (less background noise). The benefit of rRNA removal is even more obvious for amplified RNA samples.

Various methods have been applied for rRNA removal. For example, Affymetrix Inc. introduced a procedure for removing rRNA by enzymatic digestions. However, the whole procedure is both time consuming and expensive to researchers. Alternatively, mRNA may be enriched by removing rRNA molecules with magnetic beads. rRNA specific oligo probes are attached to magnetic beads, which are incubated with total RNA. In this way, rRNA is captured by the beads and later removed by centrifugation. Ambion provides a kit for the removal of bacterial RNA (MICROBExpress); the Ribo-Minus kit is available from Invitrogen for human and mouse rRNA removal. The extra step of rRNA removal introduces additional time and cost. The methods of the present invention may be used to design oligonucleotide sets that can specifically and efficiently transcribe most RNAs while having low reverse transcription efficiency for rRNAs. Thus, the amount of rRNA-derived cDNA sequences can be greatly reduced without the need for the extra steps required to remove rRNA molecules from the sample.

In contrast to the random priming strategy, oligo-d(T) is widely used to enrich the mRNA population directly. Oligo-d(T) primers anneal specifically to the poly(A) tail of mRNA molecules, and thus reverse transcription of rRNA is minimized. However, oligo-d(T) primers are not suitable for all applications. For example, oligo-d(T) primers are not suitable as RT primers for bacterial mRNA because most of them do not have poly(A) tails. In addition, many other interesting non-coding RNAs in the transcriptome, such as miRNAs and siRNAs will not be covered. Methods and compositions relating to siRNA molecules are described, for example, in U.S. application Ser. Nos. 10/298,480, 10/360,772, 10/460,775, and 10/355,820, each of which in incorporated herein by reference. Methods and compositions relating to isolating, manipulating, and using microRNA molecules are described, for example, in U.S. application Ser. No. 10/667,126 and U.S. Application 60/575,743, each of which is incorporated herein by reference. Partially degraded RNAs also cannot be fully transcribed using oligo-d(T) primers. Degraded RNA is commonly encountered with most clinical human samples such as RNA collected from Formalin Fixed Paraffin Embedded (FFPE) samples or from tissues rich in nucleases.

In addition, the oligo-d(T) priming strategy introduces a 3' bias in cDNA synthesis because it is difficult to produce full-length cDNAs due to the limited RT extension capability. This is an especially serious problem for RT-based linear RNA amplification since only about 1 kilobase of 3' sequences can be effectively amplified. In view of this problem, most microarray platforms are designed for the 3' regions of the transcripts. For example, many Affymetrix probes are picked from the last 600 bases of the mRNA sequences. Unfortunately, this size limitation is a major drawback because researchers are unable to examine relevant biological information, such as alternative splicing, from the entire transcriptome. Whole genome tiling arrays, which are designed for profiling of the entire transcriptome, are now available. Unfortunately, most existing RNA amplification products for arrays use only oligo-d(T) primers and thus are not suitable for full-transcript coverage arrays. Oligonucleotide sets designed according to the present invention can provide full-transcript coverage because they do not anneal exclusively to poly(A) tracts and thus do not introduce a 3' bias. Of course, the inclusion of a certain amount of oligo-d(T) primers with oligonucleotide sets designed according to the present invention may be desirable to provide adequate coverage of the 3' terminus of polyadenylated RNA molecules. For example, between about 1% to 60% of the primers in a pool of primers may be oligo-d(T) primers.

The methods and compositions of the present invention provide oligonucleotide pools that can specifically and efficiently transcribe RNA, without the above-mentioned drawbacks associated with random oligonucleotide pools and oligo-d(T) pools. It will be obvious to those of skill in the art that any reverse transcriptase may be used in the present invention. In preferred embodiments, the reverse transcriptase is Moloney murine leukemia virus (MMLV) reverse transcriptase or avian myeloblastosis virus (AMV) reverse transcriptase. The reverse transcriptase may be a mutant reverse transcriptase, as long as the mutants retain cDNA synthesizing activity. Examples of reverse transcriptase mutants include those with reduced or absent RnaseH activity (e.g., Superscript™ II, Superscript™ III, and Thermo-Script™ (Invitrogen)) and those with enhanced activity at higher temperatures (Superscript™ III and ThermoScript™ (Invitrogen)). In one preferred embodiment the reverse transcriptase is Arrayscript™ (Ambion), which is a mutant MMLV with reduced RnaseH activity.

1. Stabilizing RNA

Obtaining high quality, intact RNA is important for quantitative and qualitative analysis of RNA expression. To obtain high quality RNA it is necessary to minimize the activity of RNase liberated during cell lysis and to prevent RNA degradation from other sources. This is normally accomplished by using isolation methods that disrupt tissues and inactivate or inhibit RNases simultaneously.

For specimens low in endogenous ribonuclease, isolation protocols commonly use extraction buffers containing detergents to solubilize membranes, and inhibitors of RNase such as placental ribonuclease inhibitor or vanadylribonucleoside complexes. RNA isolation from more challenging samples, such as intact tissues or cells high in endogenous ribonuclease, requires a more aggressive approach. In these cases, the tissue or cells are quickly homogenized in a powerful protein denaturant (usually guanidinium isothiocyanate) to irreversibly inactivate nucleases and solubilize cell membranes. If a tissue sample can not be promptly homogenized, it must be rapidly frozen by immersion in liquid nitrogen, and stored at −80° C. Samples frozen in this manner should not be thawed prior to RNA isolation or the RNA will be rapidly degraded by RNase liberated during the cell lysis that occurs during freezing.

RNA preservation reagents that can protect the RNA in a tissue or cell sample from nucleases at temperatures above the freezing point are also know in the art, and are described, for example, in U.S. Pat. Nos. 6,528,641 and 6,204,375, incorporated herein by reference.

2. Isolation of RNA

Methods of isolating RNA are known to those of skill in the art, and it is contemplated that any RNA isolation or purification scheme known in the art could be used in the context of the present invention. For example, Filter-based methods for the isolation of RNA are also known in the art. One example is Ambion's RNAqueous® Technology. RNAqueous® is a rapid, filter-based RNA isolation system that does not require the use of phenol, chloroform or other toxic organic chemicals.

In addition, commercially available kits such as Ambion's RiboPure™ RNA Isolation Kit, RiboPure™-Bacteria RNA Isolation Kit, and RiboPure™-Yeast RNA Isolation Kit may be used to isolate RNA. Additional methods for isolating RNA are described, for example, in U.S. application Ser. No.

09/854,412, incorporated herein by reference. Methods and compositions for isolating RNA from fixed tissues are described, for example, in U.S. Application 60/490,325, incorporated herein by reference. It is also contemplated that the chemical synthesis of RNA in situ can be used to prepare RNA.

3. Separation of DNA and RNA

In certain embodiments of the invention, it is desirable to remove DNA from RNA samples. DNA contamination can interfere with the quantitative analysis of mRNA. For example, DNA contamination can cause false positives in quantitative RT-PCR.

Methods of DNA removal from RNA samples are known to those skilled in the art. Examples of common methods include DNase digestion, acid phenol:chloroform extraction, and LiCl precipitation.

DNase is an endonuclease that cleaves DNA. It must be inactivated or removed from the reaction prior to PCR, otherwise, it may digest newly amplified DNA. Acid phenol: chloroform (5:1 phenol:CHCl$_3$; pH 4.7) extraction partitions DNA in to the organic phase. The RNA remains in the aqueous phase and can be subsequently recovered by precipitation. LiCl is a selective precipitant of RNA. It inefficiently precipitates DNA, which is discarded in the supernatant.

4. Separation of rRNA from mRNA

Ribosomal RNAs can make up as much as 80% or more of the total RNA in a sample. It is often desirable to separate mRNA from rRNA because rRNA can adversely affect the quantitative analysis of mRNA. One approach to separating rRNA from mRNA is to deplete the rRNA from the sample. One example, is the hybridization of rRNA molecules using oligonucleotides homologous to the 17S rRNA, 18S rRNA, or 28S rRNA in the case of eukaryotic rRNAs, or to the 16S rRNA or 23S rRNA in the case of bacterial rRNA. The oligonucleotides are designed such that they can be "captured" and the hybridization product removed from the sample. For example, the oligonucleotides may be immobilized on a surface such as a column or a bead. MICROBExpress™ and MICROBEnrich™ (Ambion, Austin, Tex.) are examples of commercially available kits for the depletion of rRNA. Methods and compositions for the depletion or rRNA from a sample are described in U.S. application Ser. No. 10/029,397, which is incorporated by reference. The poly(A) tail at the 3' end of most eukaryotic mRNAs can be used to separate these molecules away from rRNA and other non-mRNA species that lack this poly(A) tail.

A disadvantage of the above-mentioned methods for separating rRNA from non-rRNA sequences is that they require additional steps, which results in increased time and expense. The present invention provides methods of obtaining cDNA with substantially no contaminating rRNA-derived sequences that does not require these additional steps. One such method comprises: obtaining a pool of primers having non-identical hybridization sequences of length n, wherein the hybridization sequences are selected such that they do not substantially hybridize to an rRNA sequence; obtaining an RNA-containing sample; and combining the pool of primers and the RNA-containing sample under conditions conducive to reverse transcription of RNA in the RNA-containing sample initiated from the pool of primers; and obtaining cDNA with substantially no contaminating rRNA-derived sequences. The present invention also provides pools of oligonucleotides that efficiently transcribe cDNA from RNA sequences except for rRNA sequences. By specifically transcribing non-rRNA molecules, these primers make it unnecessary to deplete the rRNA in the sample prior to cDNA synthesis. Of course, one may deplete rRNA from a sample prior to synthesizing cDNA according to the present invention, if desired.

7. Amplification of Antisense RNA

In some embodiments, the present invention provides methods and compositions for the amplification of RNA molecules. Amplification of RNA molecules is desirable when the amount of RNA in a sample is too low for microarray analysis or other applications.

In certain aspects, the RNA is amplified by the processive synthesis of multiple RNA molecules from a single cDNA template (Eberwine amplification), which results in amplified, antisense RNA (aRNA). Methods for the synthesis of aRNA are described in U.S. Pat. Nos. 5,545,522, 5,716,785, and 5,891,636, all of which are incorporated herein by reference. Typically, these methods involve the incorporation of an RNA polymerase promoter into a cDNA molecule by priming cDNA synthesis with a oligo-d(T)/promoter sequence primer. Following synthesis of double-stranded cDNA, a reverse transcriptase is added, and antisense RNA is transcribed from the cDNA template.

The oligo-d(T) priming strategy used with conventional Eberwine amplification can introduce a 3' bias in cDNA synthesis because it is difficult to produce full-length cDNAs due to the limited RT extension capability. This limitation is a major drawback because researchers are unable to examine relevant biological information, such as alternative splicing, from the entire transcriptome. Furthermore, RNA amplification products that use only oligo-d(T) primers are not suitable for full-transcript coverage arrays. In contrast, oligonucleotide sets designed according to the present invention can provide full-transcript coverage because they do not anneal exclusively to poly(A) tracts and thus do not introduce a 3' bias. Accordingly, oligonucleotides of the present invention may be designed to contain a promoter sequence and thereby be used in the Eberwine amplification described above. Of course, the inclusion of a certain amount of oligo-d(T) primers with oligonucleotide sets designed according to the present invention may be desirable to provide adequate coverage of the 3' terminus of polyadenylated RNA molecules.

Preferably the promoter region of the amplification primer is derived from the SP6, T3, or T7 phage. The RNA polymerase used for the transcription must be capable of operably binding to the particular promoter region employed in the promoter-primer complex. A preferred RNA polymerase is that found in bacteriophages, in particular T3 and T7 phages.

8. Hybridization

As used herein, "hybridization," "hybridizes" or "capable of hybridizing" is understood to mean the forming of a double or triple stranded molecule or a molecule with partial double or triple stranded nature. The term "anneal" as used herein is synonymous with "hybridize."

It is routine for those of skill in the art to optimize hybridization conditions for particular oligonucleotides and for the desired level of specificity in the hybridization. The desired stringency for a particular hybridization reaction is often determined empirically by comparison to one or more positive or negative controls. "Stringent condition(s)" or "high stringency" are those conditions that allow hybridization between or within one or more nucleic acid strand(s) containing complementary sequence(s). Stringent conditions tolerate little, if any, mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like. Stringent conditions typically employ lower salt and/or higher temperature conditions as compared to low stringency conditions. It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride (TMAC), tetraethyl ammonium chloride (TEAC), or other salts or solvent(s) in a hybridization mixture.

Identification, isolation, or amplification of a related target nucleic acid that does not hybridize to a nucleic acid under stringent conditions may be achieved by hybridization at lower temperature and/or higher ionic strength. Such conditions are termed "low stringency" or "low stringency conditions." Of course, it is within the skill of one in the art to further modify the low or high stringency conditions to suite a particular application.

9. Nucleic Acid Arrays

The present invention provides efficient methods and compositions for the amplification of most RNA molecules from RNA-containing samples while limiting the amplification of exclusion RNA sequences. As mentioned above, an "exclusion sequence" may be any sequence or sequences to which hybridization of an oligonucleotide or pool of oligonucleotides is not desired. In the context of gene expression analysis, an exclusion sequence may be one or more abundant RNA transcripts (e.g., rRNAs and/or globin), which could interfere with the expression analysis of other sequences. By selecting primers that do not significantly transcribe exclusion sequences it is possible to increase the sensitivity of nucleic acid arrays. The term a "nucleic acid array" refers to a plurality of probe elements, each probe element comprising one or more nucleic acid molecules immobilized on one or more solid surfaces to which sample nucleic acids can be hybridized.

Microarrays are known in the art and consist of a surface to which probes that correspond in sequence to gene products (e.g., cDNAs, mRNAs, cRNAs, polypeptides, and fragments thereof), can be specifically hybridized or bound at a known position. In one embodiment, the microarray is an array (i.e., a matrix) in which each position represents a discrete binding site for an RNA, and in which binding sites are present for products of most or almost all of the genes in the organism's genome. In a preferred embodiment, the "binding site" (hereinafter, "site") is a nucleic acid or nucleic acid analogue to which a particular cognate cDNA or aRNA can specifically hybridize. The nucleic acid or analogue of the binding site can be, e.g., a synthetic oligomer, a full-length cDNA, a less-than full length cDNA, or a gene fragment. A microarray may contain binding sites for products of all or almost all genes in the target organism's genome, but such comprehensiveness is not necessarily required. Oligonucleotides that are designed according to the methods of the present invention are well suited for use with whole genome tiling arrays, exon tiling arrays, and splice variant monitoring arrays.

The nucleic acid or analogue is attached to a solid support, which may be made from glass, plastic (e.g., polypropylene, nylon), polyacrylamide, nitrocellulose, or other materials. A preferred method for attaching the nucleic acids to a surface is by printing on glass plates, as is described generally by Schena et al., 1995. See also DeRisi et al., 1996; Shalon et al., 1996; Schena et al., 1996. Each of these articles is incorporated by reference in its entirety.

Other methods for making microarrays, e.g., by masking (Fodor et al., 1991; Maskos and Southern, 1992), may also be used. In principal, any type of array, for example, dot blots on a nylon hybridization membrane (see Sambrook et al., 1989, which is incorporated in its entirety for all purposes), could be used, although, as will be recognized by those of skill in the art, very small arrays will be preferred because hybridization volumes will be smaller.

Labeled cDNA for use with arrays is typically prepared from mRNA by oligo-d(T)-primed or random-primed reverse transcription, both of which are well known in the art. As described above, however, there are disadvantages associated with both oligo-d(T) primed and random-primed reverse transcription. The methods and compositions of the present invention enable the production of labeled cDNA using designed primer pools that overcome the shortcomings associated with oligo-d(T)-primed and random-primed reverse transcription. Reverse transcription may be carried out in the presence of a dNTP conjugated to a detectable label, most preferably a fluorescently labeled dNTP. Alternatively, isolated mRNA can be converted to labeled antisense RNA synthesized by in vitro transcription of double-stranded cDNA in the presence of labeled dNTPs (Lockhart et al., 1996, which is incorporated by reference in its entirety for all purposes). In alternative embodiments, the cDNA or aRNA probe can be synthesized in the absence of detectable label and may be labeled subsequently, e.g., by incorporating biotinylated dNTPs or rNTP, or some similar means (e.g., photo-cross-linking a psoralen derivative of biotin to RNAs), followed by addition of labeled streptavidin (e.g., phycoerythrin-conjugated streptavidin) or the equivalent. Alternatively, cDNA or aRNA can be labeled indirectly by incorporation of 5-(3-aminoallyl) dNTPs or rNTPs to provide a amine reactive group for subsequent addition of label with any moiety bearing an N-Hydroxysuccinimide (NHS) ester.

Fluorescently labeled probes can be used, including suitable fluorophores such as fluorescein, lissamine, phycoerythrin, rhodamine (Perkin Elmer Cetus), Cy2, Cy3, Cy3.5, Cy5, Cy5.5, Cy7, FluorX (Amersham) and others (see, e.g., Kricka, 1992). It will be appreciated that pairs of fluorophores are chosen that have distinct emission spectra so that they can be easily distinguished. In another embodiment, a label other than a fluorescent label is used. For example, a radioactive label, or a pair of radioactive labels with distinct emission spectra, can be used (see Zhao et al., 1995; Pietu et al., 1996).

The analysis of microarray data may be accomplished using methods of statistical analysis known to those skilled in the art. For example, clustering analysis is commonly used for interpretation of microarray data. It provides both a visual representation of complex data and a method for measuring similarity between experiments. Some widely used methods for clustering microarray data include: hierarchical, K-means, and self-organizing map.

C. Kits

Any of the compositions described herein may be comprised in a kit. In a non-limiting example the kit, in suitable container means, comprises: a pool of oligonucleotide primers comprising between 15-5000 non-identical template hybridization sequences of between about 4 to 11 nucleotides in length, wherein the pool of oligonucleotides do not substantially hybridize to one or more exclusion sequences. In a preferred embodiment, the oligonucleotide primers of the kit comprise non-identical template hybridization sequences of 6 nucleotides in length. In a particularly preferred embodiment, the oligonucleotide primers of the kit comprise Sequence #s 1 to 379. In another preferred embodiment, the oligonucleotide primers of the kit comprise Sequence #s 1 to 1152. In some embodiments, the pool of oligonucleotide primers comprises between about 15-5000, 50-5000, 100-5000, 100-2500, 100-

2000, 100-1500, or 250-1500 oligonucleotide primers having non-identical template hybridization sequences, or any range derivable therein.

In certain aspects of the invention, the pool of oligonucleotide primers further comprise a promoter recognition sequence. In some aspects of the invention, the plurality of oligonucleotide primers further comprise a label. In some embodiments, the kit further comprises one or more of an oligo-d(T) primer; a reverse transcriptase; a buffer; an RNA polymerase; a single strand binding protein; ethylenediaminetetraacetic acid (EDTA); a reverse transcriptase; a dNTP mix; a ribonuclease inhibitor; a DNA polymerase; RNase H; nuclease free water; ATP; CTP; GTP; UTP; TTP; DNase I; an aRNA filter cartridge; a cDNA filter cartridge; or collection tubes. In certain embodiments the kit may also include, an rRNA depleting agent, a DNA depleting agent, labeling agents, or components for isolating poly(A) mRNA.

The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a container. The kits of the present invention also will typically include a means for containing the nucleic acids, and any other reagent containers in close confinement for commercial sale. Such containers may include cardboard containers or injection or blow-molded plastic containers into which the desired containers are retained.

When the components of the kit are provided in one or more liquid solutions, the liquid solution is an aqueous solution, with a sterile aqueous solution being preferred.

However, the components of the kit may be provided as dried powder(s). When reagents and/or components are provided as a dry powder, the powder can be reconstituted by the addition of a suitable solvent. It is envisioned that the solvent may also be provided in another container means.

Such kits may also include components that facilitate isolation of nucleic acids, such as filters, beads, or a magnetic stand. Such kits generally will comprise, in suitable means, distinct containers for each individual reagent or solution as well as for the targeting agent.

A kit will also include instructions for employing the kit components as well the use of any other reagent not included in the kit. Instructions may include variations that can be implemented.

D. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Computational Primer Design and Analysis

The following abbreviations are used in this example: RT, reverse transcription; rRNA, ribosomal ribonucleic acid; oligo, oligonucleotide; PCR, polymerase chain reaction; kb, kilobase; qPCR, quantitative polymerase chain reaction; RNA, ribonucleic acid; DNA, deoxyribonucleic acid; GAPDH, glyceraldehyde-3-phosphate dehydrogenase; $\Delta G$, free energy.

A pool of oligonucleotide primers that do not anneal to rRNA sequences but provide specific and sufficient coverage for most other RNAs were designed by computational prediction. This was achieved by feeding the rRNA sequences into a design program so that the output oligo sequences will discriminate against rRNAs. These in silico designed oligos will anneal to most transcript molecules at multiple locations to provide sufficient transcriptome coverage for cDNA synthesis.

There are three major eukaryotic rRNA sequences, 28S, 18S, and 5.8S. Combined, these sequences have 7,063 nucleotides (GenBank accession number #U13369). The complete rRNA sequences were considered in the design. Oligos of any length can be designed using the methods of the present invention. It should be taken in to consideration, however, that if the oligos are too long, the average binding sites per oligo will decrease dramatically. As a result, more oligos are needed for whole transcriptome coverage. On the other hand shorter oligos may result in less RT efficiency and less selectivity against rRNA sequences.

For this example, 6-mer oligonucleotide primers were computationally designed. The algorithm was implemented as a Perl program running on a Linux platform. The human 28S, 18S, and 5.8S rRNA sequences were downloaded from GenBank (Accession # U13369), parsed into 6-mers, and screened against all possible 6-mer sequences (4,096 total). A series of filters were applied to discriminate against those 6-mer sequences that were likely to anneal to the rRNA sequences. These filters are summarized below:

An oligo was rejected if it was found in rRNA sequences.
An oligo was retained if it had at least 2 mismatches when compared to all rRNA 6-mer sequences.
An oligo was retained if it has a single mismatch to rRNAs and this mismatch is not a GU wobble pair.
An oligo was retained if its only mismatch to rRNAs was a GU mismatch that was not at the 5' terminus of the oligo.
If the only mismatch was a GU wobble pair at the 5' end, then hits to rRNAs and perfect matches to mRNAs were considered. If the hits to rRNAs were greater than 3 or the matches to mRNAs were less than 3000, then the oligo was rejected. The hits to rRNAs were defined as the number of 3' five-base matches to rRNA sequences. The hits to mRNAs were defined as the number of occurrences of oligos perfectly matched to an mRNA sequence. Each mRNA was counted only once.
An oligo was rejected if its binding free energy ($\Delta G$) was below −8 kcal/mol.

$\Delta G$ values were used as a filter because a primer with low primer-RNA duplex stability (as measured by Gibbs free energy ($\Delta G$)) increases the likelihood of the primer mispriming to rRNA. $\Delta G$ was calculated using the nearest-neighbor method for RNA-DNA duplex (Sugimoto et al., 1995). The GU wobble filter was used because a terminal GU mismatch may not be sufficient to preventing mispriming to rRNA.

A flowchart of the computation primer design protocol is provided in FIG. 1. It should be noted, however, that the filters listed above and shown in FIG. 1 do not have to be performed in any particular order. It should also be noted that not all filters have to be used to design the oligonucleotides.

Among all possible 4096 6-mer oligos, 1152 passed all of the screening filters. The sequences of the 1152 6-mer oligonucleotides are provided in Table 1. On average, this set of 1152 primers provides 686 binding sites for one transcript. Because of the high coverage, it is possible to apply more stringent filters to further increase selectivity against rRNAs while maintaining sufficient mRNA coverage. A smaller pool with 379 oligos was obtained after excluding oligos with only a single GU wobble pair mismatch to rRNAs. This smaller pool (sequences 1 to 379 in Table 1) provides 213 binding sites per mRNA transcript on average.

This primer set can also be applied to mouse and rat RT reactions because of the very high sequence homology between human rRNAs, mouse rRNAs (NCBI Accession # BK000964), and rat rRNAs (NCBI Accession # V01270). Of the 1152 6-mer oligonucleotides selected, 1090 of them were predicted to be selective against mouse rRNAs and 1075 against rat rRNAs. Therefore, this oligo pool can be used for rRNA reduction in RT for either human, mouse or rat transcriptome.

Example 2

Primer Validation

To demonstrate that short oligonucleotides may efficiently and specifically reverse transcribe RNAs of interest, 19 gene-specific 6-mer oligonucleotides were designed for glyceraldehyde-3-phosphate dehydrogenase (GAPDH) mRNA. These primers have little sequence similarity to ribosomal RNAs. RT reactions using these primers demonstrated that GAPDH cDNA can be significantly enriched relative to rRNA cDNA. The relative cDNA synthesis yields were evaluated by real-time PCR. As shown in FIG. 3A, the 19 GAPDH-specific primers have poor RT efficiency for 18S and 28S rRNA. For the few primers that have noticeable RT efficiency for rRNAs, they have relatively low ΔG values (tighter primer-RNA binding).

The 6-mer oligos were grouped according to their RT efficiency for rRNAs. Group A contains 10 oligos with the lowest RT efficiency for rRNAs (O1, O2, O3, O5, O6, O7, O8, O9, O10, O12, and O14); Group B contains Group A+O4+O13+O15; Group C contains Group B+O16+O17+O18; Group D contains Group C+O11+O19. These oligo groups were used as RT primers in separate reactions. The GAPDH cDNA synthesis efficiency using different primer groups were compared by real-time PCR. As shown in FIG. 2B, the primer groups had RT efficiency similar to that of the positive controls (oligo dT and random hexamers).

The in silico designed oligonucleotides described in Example 1 were assessed for their RT efficiency for rRNA. Each of Sequence #s 1-379 was tested individually for its RT selectivity against 18S and 28S rRNAs. The selectivity was determined by real-time PCR. FIG. 3 shows the RT efficiency for 18S rRNA of each of the oligonucleotides. The RT efficiency of pools of the in silico designed 6-mer oligonucleotides for 18S and 28S rRNAs was also evaluated. An RT reaction with random hexamers was used as the baseline (100% RT efficiency) and was compared to reactions using other RT primers. The RT efficiency was determined with real-time PCR assays (Relative RT Efficiency (%)=2**($Ct_{N6}-Ct_{pool}$)*100%). Pool379 contained Sequence #s 1-379 and pool1152 contained Sequence #s 1-1152. As shown in FIG. 4, both pool379 and pool1152 had low RT efficiency for 18S and 28S rRNA.

RT efficiency of pool379 and pool1152 for 8 different human mRNAs was also evaluated. The 8 human genes are GAPDH, ACTB (NM_001101), COX6C (NM_004374), CPS1 (NM_001875), JUN (NM_00228), IL-18 (NM_001562), POLR2B (NM_000938), RPL13A (NM_012423). For CPS1, three PCR tests using primer pairs from different regions of the gene sequence were performed. The RT efficiency for pool379 and pool1152 was determined by real-time PCR assays (Ct values) (FIG. 5).

Reverse transcription (RT) was carried out with RETROscript System under conditions suggested by the manufacturer (Ambion). A 20 μl RT reaction contained 0.5 μg of total RNA, 2 IA of 50 μM in silico designed hexamers (random hexamers, oligo-dT as controls), 2 μl of 10× RT buffer (500 mM Tris-HCL, pH8.3, 750 mM KCl, 30 mM MgCl₂, and 50 mM DTT), 4 μl of dNTP mix (25 mM each dNTP), 1 μl of MMLV-RT (100 units/μl), 1 μl of RNase Inhibitor (10 units/μl) and Nuclease-free water. After incubation at 25° C. for 30 min and 37° C. for 1 h, the reaction mixture was incubated at 92° C. for 10 min.

Real-time PCR was performed with SYBR Green PCR Master Mix (Applied Biosystems) on an ABI Prism 7900 Sequence Detection System (Applied Biosystems) with the following conditions: 50° C. for 2 min and then at 95° C. for 10 min to activate the AmpliTaq followed by 35 cycles of amplification (95° C. for 15s; 60° C. for 30s; 72° C. for 30s). The specificity of the reactions was checked by melting curves to monitor the presence of only one duplex DNA species and by agarose gel electrophoresis analysis of certain products to confirm the amplification of a single band of the expected size.

Example 3

RNA Amplification and Microarray Analysis

The Pool379 primers were evaluated on Affymetrix Human Focus arrays. They were compared to random hexamers (N6) to determine the effect of rRNA reduction on microarray performance. Pool379, oligo dT, or N6 were tagged with T7 promoter sequences for linear amplification of total RNA. FIGS. 6A and 6B illustrate the conventional Eberwine method using oligo-dT primers and a modified Eberwine method using an in silico designed primer set such as Pool379.

The amplified RNA profiles were determined with Agilent Bioanalyzer (FIG. 7A). The profiles between Pool379 and oligo dT were very similar. In contrast, the profile of N6 was much different, with one major sharp peak between 24 and 29 seconds. This peak is likely the result of rRNA amplification. Compared to N6 primers, Pool379 primers resulted in better array correlations between technical replicates (FIGS. 7B and 7C). This is especially obvious with low signal intensity spots. The percentage of Present Calls is often used as a measurement of array sensitivity. As shown in FIG. 7D, there was a significant improvement of Present Calls when Pool379 was used as RT primers (as compared to N6).

FIG. 8 shows plots generated using the BioConductor package and were used to describe the tendency of 5' to 3' bias of Affymetrix arrays. On each chip, probe level signal intensities were averaged by probe location in all probesets. The slopes indicate the level of signal bias due to the effect of probe location. FIG. 8 shows that oligo dT was biased toward 3' probes whereas N6 and Pool379 were not. N6 and Pool379 were biased against the very 3' end, but this can be easily addressed by adding a small percentage of oligo dT to the N6 and Pool379 primers to provide coverage at the 3' end.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. application Ser. No. 09/854,412
U.S. application Ser. No. 10/029,397
U.S. application Ser. No. 10/298,480
U.S. application Ser. No. 10/355,820
U.S. application Ser. No. 10/360,772
U.S. application Ser. No. 10/460,775
U.S. application Ser. No. 10/667,126
U.S. Appln. 60/490,325
U.S. Appln. 60/575,743
U.S. Pat. No. 5,545,522
U.S. Pat. No. 5,716,785
U.S. Pat. No. 5,891,636
U.S. Pat. No. 6,204,375
U.S. Pat. No. 6,528,641
Ayyadevara et al., *Anal. Biochem.*, 284:11-18, 2000.
DeRisi et al., *Nature Genetics*, 14:457-460, 1996.
Fodor et al., *Biochemistry*, 30(33):8102-8108, 1991.
Huang et al., *Nucleic Acids Res.*, 20:4567-4573, 1992.
Hughes et al., *Nat. Biotechnol.*, 19:342-347, 2001.
Kierzek et al., *Biochemistry*, 38:14214-14223, 1999.
Kricka et al., *Clin. Chem.*, 38(12):2558-2560, 1992.
Lockhart et al., *Nat. Biotechnol.*, 14(13):1675-1680, 1996.
Maskos and Southern, *Nucleic Acids Res.*, 20(7):1679-1684, 1992.
Pietu et al., *Genome Res.*, 6(6):492-503, 1996.
Sambrook et al., *In: Molecular cloning*, Cold Spring Harbor Laboratory Press, Cold Spring Harbor, N.Y., 2001.
Sambrook et al., *In: Molecular cloning*: a laboratory manual, 2nd Ed., Cold Spring Harbor Laboratory Press, Cold Spring Harbor, N.Y., 1989.
Schena et al., *Proc. Natl. Acad. Sci. USA*, 93:10614-10619, 1996.
Schena, et al., *Science*, 270:467-470, 1995.
Shalon et al., *Genome Res.*, 6(7):639-645, 1996.
Sugimoto et al., *Biochemistry*, 34:11211-11216, 1995.
Willems et al., *J. Immunol.*, 142:2547-2554, 1989.
Zhao et al., *Gene*, 166:207-213, 1995.

What is claimed is:

1. A composition comprising a pool of oligonucleotides that do not hybridize to one or more selected sequences prepared by a process comprising:
    selecting at least one exclusion sequence to which hybridization of a pool of oligonucleotides of length n is not desired;
    identifying a set of all possible sequences of length n;
    identifying a set of all sequences of length n contained in the exclusion sequence;
    excluding from the pool of oligonucleotides those oligonucleotides of length n that are identical to a sequence of length n contained in the exclusion sequence;
    excluding from the pool of oligonucleotides those oligonucleotides in which the only mismatch is a GU at the 5' end of the sequence of length n; and
    wherein a pool of oligonucleotides of length n that do not hybridize to the exclusion sequence are identified.

2. The composition of claim 1, wherein the pool of oligonucleotides comprises between 200 to 2,000 non-identical oligonucleotides.

3. The composition of claim 1, wherein members of the pool of oligonucleotides do not hybridize to a rRNA sequence.

4. A composition comprising a pool of oligonucleotide primers comprising at least 50 non-identical template hybridization sequences of 5 to 8 nucleotides in length and comprising Sequence #s 1 to 379, wherein members of the pool of oligonucleotide primers do not hybridize to a rRNA sequence.

5. The composition of claim 4, wherein the pool of oligonucleotide primers comprises at least 300 non-identical template hybridization sequences.

6. The composition of claim 4, wherein the oligonucleotide primers further comprise a promoter recognition sequence.

7. The composition of claim 6, wherein the oligonucleotide primers further comprise a spacer sequence between the promoter recognition sequence and the template hybridization sequence.

8. The composition of claim 6, wherein the promoter recognition sequence is a T7 promoter recognition sequence.

9. The composition of claim 4 further comprising one or more of an oligo-dT primer; a reverse transcriptase; or a dNTP mix.

10. The composition of claim 4 further comprising an oligo-dT primer.

11. The composition of claim 10, wherein the ratio of the oligo-dT primer to the pool of oligonucleotide primers having non-identical template hybridization sequences between about 1:1000 to about 3:2.

12. A composition comprising a pool of oligonucleotide primers comprising at least 50 non-identical template hybridization sequences of 5 to 8 nucleotides in length and comprising Sequence #s 380 to 1152, wherein members of the pool of oligonucleotide primers do not substantially hybridize to a rRNA sequence.

13. The composition of claim 12, wherein the pool of oligonucleotide primers comprises at least 300 non-identical template hybridization sequences.

14. The composition of claim 12, wherein the oligonucleotide primers further comprise a promoter recognition sequence.

15. The composition of claim 14, wherein the oligonucleotide primers further comprise a spacer sequence between the promoter recognition sequence and the template hybridization sequence.

16. The composition of claim 14, wherein the promoter recognition sequence is a T7 promoter recognition sequence.

17. The composition of claim 12 further comprising one or more of an oligo-dT primer; a reverse transcriptase; or a dNTP mix.

18. The composition of claim 12 further comprising an oligo-dT primer.

19. The composition of claim 18, wherein the ratio of the oligo-dT primer to the pool of oligonucleotide primers having non-identical template hybridization sequences between about 1:1000 to about 3:2.

* * * * *